US012097044B2

(12) United States Patent
Hunter

(10) Patent No.: US 12,097,044 B2
(45) Date of Patent: Sep. 24, 2024

(54) DEVICES, SYSTEMS AND METHODS FOR MONITORING KNEE REPLACEMENTS

(71) Applicant: Canary Medical Inc., Vancouver (CA)

(72) Inventor: William L. Hunter, Vancouver (CA)

(73) Assignee: Canary Medical Inc., Vancouver (CA)

( * ) Notice: Subject to any disclaimer, the term of this patent is extended or adjusted under 35 U.S.C. 154(b) by 385 days.

(21) Appl. No.: 16/459,377

(22) Filed: Jul. 1, 2019

(65) Prior Publication Data

US 2019/0388025 A1    Dec. 26, 2019

Related U.S. Application Data

(63) Continuation of application No. 14/392,173, filed as application No. PCT/US2014/043736 on Jun. 23, 2014, now abandoned.

(60) Provisional application No. 61/838,317, filed on Jun. 23, 2013.

(51) Int. Cl.
| | |
|---|---|
| A61F 2/38 | (2006.01) |
| A61B 5/00 | (2006.01) |
| A61B 5/01 | (2006.01) |
| A61B 5/11 | (2006.01) |
| A61F 2/46 | (2006.01) |
| A61F 2/30 | (2006.01) |
| A61F 2/48 | (2006.01) |

(52) U.S. Cl.
CPC .......... *A61B 5/4851* (2013.01); *A61B 5/0031* (2013.01); *A61B 5/01* (2013.01); *A61B 5/11* (2013.01); *A61B 5/112* (2013.01); *A61B 5/4528* (2013.01); *A61B 5/4585* (2013.01); *A61B 5/686* (2013.01); *A61F 2/38* (2013.01); *A61F 2/3859* (2013.01); *A61F 2/3877* (2013.01); *A61F 2/389* (2013.01); *A61F 2/4657* (2013.01); *A61B 2562/0219* (2013.01); *A61F 2002/3067* (2013.01); *A61F 2002/4631* (2013.01); *A61F 2002/4666* (2013.01); *A61F 2002/4668* (2013.01); *A61F 2002/4674* (2013.01); *A61F 2/488* (2021.08)

(58) Field of Classification Search
None
See application file for complete search history.

(56) References Cited

U.S. PATENT DOCUMENTS

| | | | |
|---|---|---|---|
| 4,161,782 | A | 7/1979 | McCracken |
| 4,894,728 | A | 1/1990 | Goodman |
| 5,019,794 | A | 5/1991 | Letessier et al. |
| 5,042,504 | A | 8/1991 | Huberti |
| 5,245,109 | A | 9/1993 | Kaminsky et al. |

(Continued)

FOREIGN PATENT DOCUMENTS

| | | | |
|---|---|---|---|
| AT | 513434 B1 | 2/2015 | |
| CA | 1212501 A | 10/1986 | |

(Continued)

OTHER PUBLICATIONS

PCT International Search Report and Written Opinion dated Oct. 30, 2020, for PCT/US2020/036516.

(Continued)

*Primary Examiner* — Megan Y Wolf

(57) ABSTRACT

Knee replacement prosthesis are provided, comprising a plurality of sensors and at least one of a femoral component, a patellar prosthesis and a tibial component.

12 Claims, 9 Drawing Sheets

(56) References Cited

U.S. PATENT DOCUMENTS

| | | | |
|---|---|---|---|
| 5,312,216 A * | 5/1994 | Hogg | A61F 2/3854 623/22.4 |
| 5,358,202 A | 10/1994 | Tse et al. | |
| 5,383,874 A | 1/1995 | Jackson | |
| 5,413,604 A | 5/1995 | Hodge | |
| 5,626,581 A | 5/1997 | Staehlin et al. | |
| 5,672,954 A | 9/1997 | Watanabe | |
| 5,716,981 A | 2/1998 | Hunter et al. | |
| 5,833,603 A | 11/1998 | Kovacs et al. | |
| H1765 H | 12/1998 | O'Phelan | |
| 5,906,643 A | 5/1999 | Walker | |
| 6,019,794 A | 2/2000 | Walker | |
| 6,206,835 B1 | 3/2001 | Spillman, Jr. et al. | |
| 6,245,109 B1 | 6/2001 | Mendes et al. | |
| 6,358,202 B1 | 3/2002 | Arent | |
| 6,374,097 B1 | 4/2002 | Kudou | |
| 6,447,448 B1 | 9/2002 | Ishikawa | |
| 6,610,096 B2 | 8/2003 | MacDonald | |
| 6,610,101 B2 | 8/2003 | Herr et al. | |
| 6,620,168 B1 | 9/2003 | Lombardo et al. | |
| 6,706,071 B1 | 3/2004 | Wolter | |
| 6,712,778 B1 | 3/2004 | Jeffcoat et al. | |
| 6,805,667 B2 | 10/2004 | Christopherson | |
| 7,009,511 B2 | 3/2006 | Mazar et al. | |
| 7,097,662 B2 | 8/2006 | Evans, III et al. | |
| 7,127,300 B2 | 10/2006 | Mazar et al. | |
| 7,130,695 B2 | 10/2006 | Czygan et al. | |
| 7,141,026 B2 | 11/2006 | Aminian et al. | |
| 7,190,273 B2 | 3/2007 | Liao et al. | |
| 7,195,645 B2 | 3/2007 | DiSilvestro et al. | |
| 7,328,131 B2 | 2/2008 | Donofrio et al. | |
| 7,333,013 B2 | 2/2008 | Berger | |
| 7,347,874 B2 | 3/2008 | DiSilvestro | |
| 7,383,071 B1 | 6/2008 | Russell et al. | |
| 7,450,332 B2 | 11/2008 | Pasolini et al. | |
| 7,463,997 B2 | 12/2008 | Pasolini et al. | |
| 7,553,923 B2 | 6/2009 | Williams et al. | |
| 7,559,951 B2 | 7/2009 | DiSilvestro et al. | |
| 7,603,894 B2 | 10/2009 | Breed | |
| 7,613,497 B2 | 11/2009 | Govari et al. | |
| 7,813,808 B1 | 10/2010 | Doron et al. | |
| 7,819,808 B2 | 10/2010 | Oonuki | |
| 7,874,673 B2 | 1/2011 | Shinohara et al. | |
| 7,889,070 B2 | 2/2011 | Reeves | |
| 7,922,771 B2 | 4/2011 | Otto et al. | |
| 7,924,267 B2 | 4/2011 | Sirtori | |
| 8,029,566 B2 | 10/2011 | Lozier et al. | |
| 8,080,064 B2 | 12/2011 | Dietz et al. | |
| 8,109,890 B2 | 2/2012 | Kamiar et al. | |
| 8,176,922 B2 | 5/2012 | Sherman et al. | |
| 8,241,296 B2 | 8/2012 | Wasielewski | |
| 8,244,368 B2 | 8/2012 | Sherman et al. | |
| 8,245,583 B2 | 8/2012 | Stein | |
| 8,283,793 B2 | 10/2012 | Pless | |
| 8,311,632 B2 | 11/2012 | Pless et al. | |
| 8,317,869 B2 | 11/2012 | Cloutier et al. | |
| 8,372,420 B2 | 2/2013 | Hunter et al. | |
| 8,491,569 B1 | 7/2013 | Anderson | |
| 8,551,023 B2 | 10/2013 | Sherman et al. | |
| 8,556,888 B2 | 10/2013 | Nields et al. | |
| 8,634,928 B1 | 1/2014 | O'Driscoll et al. | |
| 8,721,643 B2 | 5/2014 | Morgan et al. | |
| 8,761,859 B2 | 6/2014 | Roche | |
| 8,876,739 B2 | 11/2014 | Salarian et al. | |
| 8,996,892 B1 | 3/2015 | Chu et al. | |
| 9,019,098 B2 | 4/2015 | Okano | |
| 9,307,932 B2 | 4/2016 | Mariani et al. | |
| 9,364,659 B1 | 6/2016 | Rao | |
| 9,368,105 B1 | 6/2016 | Freed et al. | |
| 9,390,724 B2 | 7/2016 | List | |
| 9,393,433 B2 | 7/2016 | Parramon et al. | |
| 9,424,840 B1 | 8/2016 | Hart et al. | |
| 9,445,930 B2 | 9/2016 | Chen et al. | |
| 9,451,919 B2 | 9/2016 | Roche | |
| 9,456,915 B2 | 10/2016 | Chen et al. | |
| 9,549,742 B2 | 1/2017 | Berend et al. | |
| 9,629,583 B2 | 4/2017 | Gradel | |
| 9,820,858 B2 | 11/2017 | Harris et al. | |
| 10,070,973 B2 | 9/2018 | Sherman et al. | |
| 10,219,699 B2 | 3/2019 | Wilder et al. | |
| 10,285,637 B1 | 5/2019 | Hnat et al. | |
| 10,492,686 B2 | 12/2019 | Hunter et al. | |
| 10,499,855 B2 | 12/2019 | Hunter | |
| 10,582,896 B2 | 3/2020 | Revie | |
| 10,596,009 B2 | 3/2020 | Mines et al. | |
| 11,071,279 B2 | 7/2021 | Singh et al. | |
| 11,191,479 B2 | 12/2021 | Bailey et al. | |
| 2001/0032059 A1 | 10/2001 | Kelly et al. | |
| 2001/0050087 A1 | 12/2001 | Weissman et al. | |
| 2002/0024450 A1 | 2/2002 | Townsend et al. | |
| 2002/0026224 A1 | 2/2002 | Thompson | |
| 2002/0107576 A1 | 8/2002 | Meyers et al. | |
| 2002/0113685 A1 | 8/2002 | Izaki et al. | |
| 2002/0147416 A1 | 10/2002 | Zogbi et al. | |
| 2003/0004403 A1 | 1/2003 | Drinan et al. | |
| 2003/0069644 A1 | 4/2003 | Kovacevic et al. | |
| 2003/0204267 A1 | 10/2003 | Hazebrouck et al. | |
| 2004/0011137 A1 | 1/2004 | Hnat et al. | |
| 2004/0019382 A1 | 1/2004 | Amirouche et al. | |
| 2004/0019384 A1 | 1/2004 | Kirking | |
| 2004/0083003 A1 | 4/2004 | Wasielewski | |
| 2004/0113790 A1 | 6/2004 | Hamel | |
| 2004/0138757 A1 | 7/2004 | Nadzadi et al. | |
| 2004/0204635 A1 | 10/2004 | Scharf et al. | |
| 2004/0204766 A1 | 10/2004 | Siebel | |
| 2004/0211580 A1 | 10/2004 | Wang et al. | |
| 2004/0243148 A1 | 12/2004 | Wasielewski | |
| 2004/0243244 A1 | 12/2004 | Otto et al. | |
| 2004/0249464 A1 | 12/2004 | Bindseil et al. | |
| 2004/0249471 A1 | 12/2004 | Bindseil et al. | |
| 2005/0010299 A1 | 1/2005 | Disilvestro | |
| 2005/0010301 A1 | 1/2005 | Disilvestro | |
| 2005/0012610 A1 | 1/2005 | Liao et al. | |
| 2005/0021126 A1 | 1/2005 | Machan et al. | |
| 2005/0027192 A1 | 2/2005 | Govari et al. | |
| 2005/0065408 A1 | 3/2005 | Benderev | |
| 2005/0165317 A1 | 7/2005 | Turner et al. | |
| 2005/0171594 A1 | 8/2005 | Machan et al. | |
| 2005/0181005 A1 | 8/2005 | Hunter et al. | |
| 2005/0181009 A1 | 8/2005 | Hunter et al. | |
| 2005/0228410 A1 | 10/2005 | Berreklouw | |
| 2005/0242666 A1 | 11/2005 | Huscher et al. | |
| 2005/0245992 A1 | 11/2005 | Persen et al. | |
| 2005/0288563 A1 | 12/2005 | Feliss et al. | |
| 2006/0009856 A1 | 1/2006 | Sherman | |
| 2006/0030771 A1 | 2/2006 | Levine et al. | |
| 2006/0030945 A1 | 2/2006 | Wright | |
| 2006/0036246 A1 | 2/2006 | Carl et al. | |
| 2006/0047283 A1 * | 3/2006 | Evans, III | A61B 5/412 623/20.2 |
| 2006/0069403 A1 | 3/2006 | Shalon et al. | |
| 2006/0111777 A1 | 5/2006 | Chen | |
| 2006/0116744 A1 | 6/2006 | Von Arx et al. | |
| 2006/0142670 A1 | 6/2006 | DiSilvestro | |
| 2006/0152377 A1 * | 7/2006 | Beebe | A43B 3/34 340/665 |
| 2006/0165317 A1 | 7/2006 | Gzybowski | |
| 2006/0184067 A1 | 8/2006 | Clark et al. | |
| 2006/0224088 A1 | 10/2006 | Roche | |
| 2006/0229711 A1 | 10/2006 | Yan et al. | |
| 2006/0229730 A1 | 10/2006 | Railey et al. | |
| 2006/0271112 A1 | 11/2006 | Martinson | |
| 2006/0271199 A1 * | 11/2006 | Johnson | A61F 2/4657 600/431 |
| 2006/0282168 A1 | 12/2006 | Sherman et al. | |
| 2007/0004994 A1 | 1/2007 | Sherman | |
| 2007/0005141 A1 | 1/2007 | Sherman | |
| 2007/0034013 A1 | 2/2007 | Moon et al. | |
| 2007/0060955 A1 | 3/2007 | Strother et al. | |
| 2007/0067018 A1 | 3/2007 | Miller | |
| 2007/0088442 A1 | 4/2007 | Cima et al. | |
| 2007/0089518 A1 | 4/2007 | Ericson et al. | |
| 2007/0126696 A1 | 6/2007 | Boillot | |
| 2007/0151884 A1 | 7/2007 | Thoes et al. | |

(56) References Cited

U.S. PATENT DOCUMENTS

| | | |
|---|---|---|
| 2007/0161884 A1 | 7/2007 | Black |
| 2007/0167809 A1 | 7/2007 | Dala-Krishna |
| 2007/0179628 A1 | 8/2007 | Rochetin |
| 2007/0179739 A1 | 8/2007 | Donofrio et al. |
| 2007/0211022 A1 | 9/2007 | Boillot |
| 2007/0211023 A1 | 9/2007 | Boillot |
| 2007/0233065 A1* | 10/2007 | Donofrio ............ A61B 8/4472 606/309 |
| 2007/0233267 A1 | 10/2007 | Amirouche et al. |
| 2007/0234819 A1 | 10/2007 | Amirouche |
| 2007/0238984 A1 | 10/2007 | Maschke et al. |
| 2007/0238992 A1 | 10/2007 | Donofrio et al. |
| 2007/0239282 A1 | 10/2007 | Clayton, III et al. |
| 2007/0265662 A1 | 11/2007 | Ufford |
| 2007/0288194 A1 | 12/2007 | Boillot |
| 2008/0020012 A1 | 1/2008 | Ju et al. |
| 2008/0027679 A1 | 1/2008 | Shklarski |
| 2008/0033527 A1 | 2/2008 | Nunez et al. |
| 2008/0048878 A1 | 2/2008 | Boillot |
| 2008/0065225 A1 | 3/2008 | Wasielewski |
| 2008/0076972 A1 | 3/2008 | Dorogusker et al. |
| 2008/0088436 A1 | 4/2008 | Reeves et al. |
| 2008/0114270 A1 | 5/2008 | DiSilvestro et al. |
| 2008/0139954 A1 | 6/2008 | Day et al. |
| 2008/0214903 A1 | 9/2008 | Orbach |
| 2008/0215609 A1 | 9/2008 | Cleveland et al. |
| 2008/0235621 A1 | 9/2008 | Boillot |
| 2008/0275350 A1 | 11/2008 | Liao et al. |
| 2008/0300597 A1 | 12/2008 | Morgan |
| 2008/0300659 A1 | 12/2008 | Matos |
| 2008/0306325 A1 | 12/2008 | Burnett et al. |
| 2008/0309481 A1 | 12/2008 | Tanaka et al. |
| 2009/0005708 A1 | 1/2009 | Johanson et al. |
| 2009/0005876 A1 | 1/2009 | Dietz |
| 2009/0012372 A1 | 1/2009 | Burnett et al. |
| 2009/0048524 A1 | 2/2009 | Wildau |
| 2009/0076358 A1 | 3/2009 | Reggiardo et al. |
| 2009/0088756 A1 | 4/2009 | Anderson |
| 2009/0099570 A1 | 4/2009 | Paradis et al. |
| 2009/0119222 A1 | 5/2009 | O'Neil |
| 2009/0149964 A1 | 6/2009 | May et al. |
| 2009/0157146 A1 | 6/2009 | Linder et al. |
| 2009/0192533 A1 | 7/2009 | Dlugos, Jr. et al. |
| 2009/0253587 A1 | 10/2009 | Fernandez |
| 2009/0264894 A1 | 10/2009 | Wasielewski |
| 2009/0299228 A1 | 12/2009 | Lozier et al. |
| 2010/0014626 A1 | 1/2010 | Fennell et al. |
| 2010/0057046 A1 | 3/2010 | Stevens et al. |
| 2010/0100011 A1 | 4/2010 | Roche |
| 2010/0145337 A1 | 6/2010 | Janna et al. |
| 2010/0152621 A1 | 6/2010 | Janna |
| 2010/0164705 A1 | 7/2010 | Blanchard |
| 2010/0191100 A1 | 7/2010 | Anderson et al. |
| 2010/0204551 A1 | 8/2010 | Roche |
| 2010/0204802 A1 | 8/2010 | Wilson et al. |
| 2010/0204955 A1 | 8/2010 | Roche et al. |
| 2010/0249533 A1 | 9/2010 | Pierce et al. |
| 2010/0249787 A1 | 9/2010 | Roche |
| 2010/0249790 A1 | 9/2010 | Roche |
| 2010/0250284 A1 | 9/2010 | Roche et al. |
| 2010/0262160 A1 | 10/2010 | Boyden et al. |
| 2010/0285082 A1 | 11/2010 | Fernandez |
| 2010/0287422 A1 | 11/2010 | Miyazaki |
| 2010/0312188 A1 | 12/2010 | Robertson et al. |
| 2010/0326187 A1 | 12/2010 | Stein |
| 2010/0326194 A1 | 12/2010 | Stein et al. |
| 2010/0326210 A1 | 12/2010 | Stein et al. |
| 2010/0326211 A1 | 12/2010 | Stein |
| 2010/0327848 A1 | 12/2010 | Stein |
| 2010/0327880 A1 | 12/2010 | Stein |
| 2010/0328077 A1 | 12/2010 | Stein |
| 2010/0328098 A1 | 12/2010 | Stein et al. |
| 2010/0331663 A1 | 12/2010 | Stein |
| 2010/0331679 A1 | 12/2010 | Stein |
| 2010/0331680 A1 | 12/2010 | Stein |
| 2010/0331681 A1 | 12/2010 | Stein et al. |
| 2010/0331682 A1 | 12/2010 | Stein et al. |
| 2010/0331685 A1 | 12/2010 | Stein et al. |
| 2010/0331687 A1 | 12/2010 | Stein et al. |
| 2010/0331704 A1 | 12/2010 | Stein et al. |
| 2010/0331718 A1 | 12/2010 | Stein |
| 2010/0331733 A1 | 12/2010 | Stein |
| 2010/0331734 A1 | 12/2010 | Stein |
| 2010/0331738 A1 | 12/2010 | Stein et al. |
| 2010/0331894 A1 | 12/2010 | Stein |
| 2010/0331932 A1 | 12/2010 | Stevenson et al. |
| 2010/0332152 A1 | 12/2010 | Stein |
| 2011/0004076 A1 | 1/2011 | Janna et al. |
| 2011/0015693 A1 | 1/2011 | Williamson |
| 2011/0019595 A1 | 1/2011 | Magar et al. |
| 2011/0054272 A1 | 3/2011 | Derchak |
| 2011/0060220 A1 | 3/2011 | Roche et al. |
| 2011/0063094 A1 | 3/2011 | Meiertoberens et al. |
| 2011/0077736 A1 | 3/2011 | Rofougaran |
| 2011/0077865 A1 | 3/2011 | Chen et al. |
| 2011/0087306 A1 | 4/2011 | Goossen |
| 2011/0092860 A1* | 4/2011 | Salarian ............... A61B 5/6831 600/595 |
| 2011/0092948 A1 | 4/2011 | Shachar et al. |
| 2011/0098576 A1 | 4/2011 | Hollstien |
| 2011/0158206 A1 | 6/2011 | Shrestha et al. |
| 2011/0160572 A1 | 6/2011 | McIntosh et al. |
| 2011/0160583 A1 | 6/2011 | Roche et al. |
| 2011/0160616 A1 | 6/2011 | Stein et al. |
| 2011/0184740 A1 | 7/2011 | Gruenstein et al. |
| 2011/0196501 A1 | 8/2011 | Michelson |
| 2011/0200052 A1 | 8/2011 | Mungo |
| 2011/0213221 A1 | 9/2011 | Roche |
| 2011/0213413 A1 | 9/2011 | Brown et al. |
| 2011/0224564 A1 | 9/2011 | Moon et al. |
| 2011/0288436 A1 | 11/2011 | Stone |
| 2011/0288805 A1 | 11/2011 | Aminian et al. |
| 2011/0319755 A1 | 12/2011 | Stein et al. |
| 2012/0029316 A1 | 2/2012 | Raptis et al. |
| 2012/0035868 A1 | 2/2012 | Roche et al. |
| 2012/0095526 A1 | 4/2012 | Roche |
| 2012/0116310 A1 | 5/2012 | Forsell |
| 2012/0123498 A1 | 5/2012 | Gross |
| 2012/0123716 A1 | 5/2012 | Clark |
| 2012/0130687 A1 | 5/2012 | Otto et al. |
| 2012/0152017 A1 | 6/2012 | Stein et al. |
| 2012/0157839 A1 | 6/2012 | Stein |
| 2012/0157884 A1 | 6/2012 | Stein |
| 2012/0166680 A1 | 6/2012 | Masoud et al. |
| 2012/0190940 A1 | 7/2012 | Stein et al. |
| 2012/0191206 A1 | 7/2012 | Stein et al. |
| 2012/0216611 A1 | 8/2012 | Stein |
| 2012/0220839 A1 | 8/2012 | Stein et al. |
| 2012/0226360 A1 | 9/2012 | Stein et al. |
| 2012/0226364 A1 | 9/2012 | Kampas et al. |
| 2012/0232834 A1 | 9/2012 | Roche et al. |
| 2012/0283600 A1 | 11/2012 | Stein |
| 2012/0313760 A1 | 12/2012 | Okano |
| 2012/0323333 A1 | 12/2012 | Metzger |
| 2012/0330367 A1 | 12/2012 | Roche et al. |
| 2013/0011008 A1 | 1/2013 | Ikezoye et al. |
| 2013/0023794 A1 | 1/2013 | Stein et al. |
| 2013/0027186 A1 | 1/2013 | Cinbis et al. |
| 2013/0079668 A1 | 3/2013 | Stein et al. |
| 2013/0079669 A1 | 3/2013 | Stein et al. |
| 2013/0079670 A1 | 3/2013 | Stein et al. |
| 2013/0079671 A1 | 3/2013 | Stein et al. |
| 2013/0079672 A1 | 3/2013 | Stein et al. |
| 2013/0079674 A1 | 3/2013 | Stein et al. |
| 2013/0079675 A1 | 3/2013 | Stein et al. |
| 2013/0079679 A1 | 3/2013 | Roche et al. |
| 2013/0079790 A1 | 3/2013 | Stein et al. |
| 2013/0079884 A1 | 3/2013 | Stein et al. |
| 2013/0109998 A1 | 5/2013 | Swoboda et al. |
| 2013/0110008 A1 | 5/2013 | Bourget et al. |
| 2013/0123684 A1 | 5/2013 | Giuffrida et al. |
| 2013/0144379 A1 | 6/2013 | Najafi et al. |
| 2013/0023795 A1 | 7/2013 | Stein |
| 2013/0179110 A1 | 7/2013 | Lee |

(56) References Cited

U.S. PATENT DOCUMENTS

| | | |
|---|---|---|
| 2013/0197656 A1 | 8/2013 | Conrad |
| 2013/0215979 A1 | 8/2013 | Yakovlev et al. |
| 2013/0225949 A1 | 8/2013 | Roche |
| 2013/0225982 A1 | 8/2013 | McIntosh et al. |
| 2013/0226034 A1 | 8/2013 | Stein et al. |
| 2013/0226035 A1 | 8/2013 | Stein et al. |
| 2013/0252610 A1 | 9/2013 | Kim |
| 2013/0261450 A1 | 10/2013 | Stein et al. |
| 2013/0268081 A1 | 10/2013 | Stein |
| 2013/0281839 A1 | 10/2013 | Yan et al. |
| 2013/0317367 A1 | 11/2013 | Shuler |
| 2013/0325019 A1 | 12/2013 | Thomas et al. |
| 2013/0338455 A1 | 12/2013 | Gradel et al. |
| 2013/0338770 A1 | 12/2013 | Boyden et al. |
| 2014/0009262 A1 | 1/2014 | Robertson et al. |
| 2014/0025338 A1 | 1/2014 | Blount et al. |
| 2014/0031063 A1 | 1/2014 | Park et al. |
| 2014/0058289 A1 | 2/2014 | Panken et al. |
| 2014/0085102 A1 | 3/2014 | McCormick |
| 2014/0094715 A1 | 4/2014 | Stein et al. |
| 2014/0107796 A1 | 4/2014 | Stein |
| 2014/0135589 A1 | 5/2014 | Osorio |
| 2014/0135616 A1 | 5/2014 | Stein et al. |
| 2014/0135624 A1 | 5/2014 | Stein et al. |
| 2014/0135655 A1 | 5/2014 | Stein et al. |
| 2014/0135773 A1 | 5/2014 | Stein et al. |
| 2014/0136143 A1 | 5/2014 | Stein |
| 2014/0148676 A1 | 5/2014 | Stein et al. |
| 2014/0163645 A1 | 6/2014 | Dinsmoor et al. |
| 2014/0171754 A1 | 6/2014 | Stein et al. |
| 2014/0180697 A1 | 6/2014 | Torok et al. |
| 2014/0188007 A1 | 7/2014 | Stein |
| 2014/0194707 A1 | 7/2014 | Stein et al. |
| 2014/0200584 A1 | 7/2014 | Stein et al. |
| 2014/0213867 A1 | 7/2014 | Pletcher et al. |
| 2014/0256324 A1 | 9/2014 | Mohanty |
| 2014/0257047 A1 | 9/2014 | Sillay et al. |
| 2014/0275815 A1 | 9/2014 | Stein et al. |
| 2014/0275849 A1 | 9/2014 | Acquista |
| 2014/0275861 A1 | 9/2014 | Kroh et al. |
| 2014/0276240 A1 | 9/2014 | Stein et al. |
| 2014/0276241 A1 | 9/2014 | Stein |
| 2014/0276885 A1 | 9/2014 | Stein et al. |
| 2014/0276887 A1 | 9/2014 | Stein et al. |
| 2014/0277542 A1 | 9/2014 | Stein et al. |
| 2014/0288464 A1 | 9/2014 | Stein |
| 2014/0296663 A1 | 10/2014 | Boyden et al. |
| 2014/0303739 A1 | 10/2014 | Mentink et al. |
| 2014/0322935 A1 | 10/2014 | Filman et al. |
| 2014/0328253 A1 | 11/2014 | Lee |
| 2014/0330105 A1 | 11/2014 | Roche |
| 2014/0378872 A1 | 12/2014 | Hong et al. |
| 2015/0032215 A1 | 1/2015 | Slamin et al. |
| 2015/0032217 A1 | 1/2015 | Bojarski |
| 2015/0039093 A1 | 2/2015 | McTighe et al. |
| 2015/0057775 A1 | 2/2015 | Dong |
| 2015/0080901 A1 | 3/2015 | Stein |
| 2015/0088253 A1 | 3/2015 | Doll et al. |
| 2015/0124675 A1 | 5/2015 | Farmer et al. |
| 2015/0164401 A1 | 6/2015 | Toth et al. |
| 2015/0202494 A1 | 7/2015 | Hollenbach et al. |
| 2015/0238304 A1 | 8/2015 | Lamraoui |
| 2015/0238691 A1 | 8/2015 | Boyden et al. |
| 2015/0335290 A1 | 11/2015 | Hunter |
| 2016/0025978 A1 | 1/2016 | Mallinson |
| 2016/0029952 A1 | 2/2016 | Hunter |
| 2016/0029998 A1 | 2/2016 | Brister et al. |
| 2016/0038087 A1 | 2/2016 | Hunter |
| 2016/0051823 A1 | 2/2016 | Maile et al. |
| 2016/0081762 A1 | 3/2016 | Stein et al. |
| 2016/0101281 A1 | 4/2016 | Chen |
| 2016/0106533 A1 | 4/2016 | Galstian et al. |
| 2016/0128573 A1 | 5/2016 | Wilder et al. |
| 2016/0166201 A1 | 6/2016 | Stein |
| 2016/0192878 A1 | 7/2016 | Hunter |
| 2016/0199658 A1 | 7/2016 | Nassif et al. |
| 2016/0232322 A1 | 8/2016 | Mensinger et al. |
| 2016/0302721 A1 | 10/2016 | Wiedenhoefer et al. |
| 2016/0310077 A1 | 10/2016 | Hunter |
| 2016/0338644 A1 | 11/2016 | Connor |
| 2016/0340177 A1 | 11/2016 | Takada |
| 2016/0374566 A1 | 12/2016 | Fung et al. |
| 2017/0035593 A1 | 2/2017 | Chen et al. |
| 2017/0049963 A1 | 2/2017 | Varsavsky et al. |
| 2017/0119316 A1 | 5/2017 | Herrmann et al. |
| 2017/0119472 A1 | 5/2017 | Herrmann et al. |
| 2017/0119566 A1 | 5/2017 | Chen et al. |
| 2017/0138986 A1 | 5/2017 | Kern |
| 2017/0156288 A1 | 6/2017 | Singh |
| 2017/0156632 A1 | 6/2017 | Swiston et al. |
| 2017/0181825 A1 | 6/2017 | Hunter |
| 2017/0189553 A1 | 7/2017 | Hunter |
| 2017/0196478 A1 | 7/2017 | Hunter |
| 2017/0196499 A1 | 7/2017 | Hunter |
| 2017/0196507 A1 | 7/2017 | Singh et al. |
| 2017/0196508 A1 | 7/2017 | Hunter |
| 2017/0196509 A1 | 7/2017 | Hunter |
| 2017/0252187 A1 | 9/2017 | Chapman et al. |
| 2017/0294949 A1 | 10/2017 | Zhang et al. |
| 2017/0328931 A1 | 11/2017 | Zhang et al. |
| 2017/0333080 A1 | 11/2017 | Roschak et al. |
| 2018/0000380 A1 | 1/2018 | Stein et al. |
| 2018/0028824 A1 | 2/2018 | Pivonka et al. |
| 2018/0055443 A1 | 3/2018 | Stein et al. |
| 2018/0064335 A1 | 3/2018 | Rutschman et al. |
| 2018/0125365 A1 | 5/2018 | Hunter et al. |
| 2018/0177607 A1 | 6/2018 | Trabish et al. |
| 2018/0177611 A1 | 6/2018 | Trabish et al. |
| 2018/0177612 A1 | 6/2018 | Trabish et al. |
| 2018/0228428 A1 | 8/2018 | Anker et al. |
| 2018/0235546 A1 | 8/2018 | Hunter |
| 2019/0038361 A1 | 2/2019 | Wasielewski |
| 2019/0038425 A1 | 2/2019 | Otto et al. |
| 2019/0076033 A1 | 3/2019 | Sweeney et al. |
| 2019/0076273 A1 | 3/2019 | Goodchild et al. |
| 2019/0192072 A1 | 6/2019 | Bailey et al. |
| 2019/0231555 A1 | 8/2019 | Neubardt |
| 2019/0247197 A1 | 8/2019 | Jagannathan et al. |
| 2019/0290451 A1 | 9/2019 | Trabish et al. |
| 2019/0350518 A1 | 11/2019 | Bailey et al. |
| 2019/0350519 A1 | 11/2019 | Bailey et al. |
| 2019/0350520 A1 | 11/2019 | Bailey et al. |
| 2019/0350521 A1 | 11/2019 | Bailey et al. |
| 2019/0350522 A1 | 11/2019 | Bailey et al. |
| 2019/0350523 A1 | 11/2019 | Bailey et al. |
| 2020/0054215 A1 | 2/2020 | Roche |
| 2020/0093430 A1 | 3/2020 | Bailey et al. |
| 2020/0093431 A1 | 3/2020 | Bailey et al. |
| 2020/0155327 A1 | 5/2020 | Suh et al. |
| 2021/0077241 A1 | 3/2021 | Hunter |

FOREIGN PATENT DOCUMENTS

| | | |
|---|---|---|
| CA | 2620247 A1 | 3/2007 |
| CA | 3017932 A1 | 9/2017 |
| CN | 2580920 Y | 10/2003 |
| CN | 1806776 A | 7/2006 |
| CN | 1899222 | 1/2007 |
| CN | 101060815 A | 10/2007 |
| CN | 101254103 A | 9/2008 |
| CN | 101257860 A | 9/2008 |
| CN | 101273925 A | 10/2008 |
| CN | 101287408 A | 10/2008 |
| CN | 101296673 A | 10/2008 |
| CN | 101426453 A | 5/2009 |
| CN | 101484085 A | 7/2009 |
| CN | 101495025 | 7/2009 |
| CN | 101536938 A | 9/2009 |
| CN | 101573085 A | 11/2009 |
| CN | 101773387 | 7/2010 |
| CN | 101849865 A | 10/2010 |
| CN | 202207217 | 11/2011 |
| CN | 101773387 B | 12/2011 |
| CN | 102688097 A | 9/2012 |

(56) References Cited

FOREIGN PATENT DOCUMENTS

| | | |
|---|---|---|
| CN | 102740803 A | 10/2012 |
| CN | 102885626 A | 1/2013 |
| CN | 102905649 A | 1/2013 |
| CN | 103313661 A | 9/2013 |
| CN | 103458830 A | 12/2013 |
| CN | 103735303 A | 4/2014 |
| CN | 103957992 A | 7/2014 |
| CN | 105283150 A | 1/2016 |
| CN | 109310324 A | 2/2019 |
| DE | 4322619 C1 | 9/1994 |
| DE | 19924676 | 11/2000 |
| DE | 10342823 A1 | 4/2005 |
| EP | 1528902 B1 | 11/2006 |
| EP | 2018825 | 1/2009 |
| EP | 1814471 | 3/2010 |
| EP | 2967879 B1 | 1/2022 |
| JP | 2001046411 A | 2/2001 |
| JP | 2003527926 A | 9/2003 |
| JP | 2005520630 | 7/2005 |
| JP | 2005288172 A | 10/2005 |
| JP | 2006055629 | 3/2006 |
| JP | 2006102498 A | 4/2006 |
| JP | 2007083019 A | 4/2007 |
| JP | 2007535372 | 12/2007 |
| JP | 2008501488 A | 1/2008 |
| JP | 2008510584 A | 4/2008 |
| JP | 2011514812 | 5/2011 |
| JP | 2013039444 A | 2/2013 |
| JP | 2016525389 A | 8/2016 |
| JP | 2017023436 A | 2/2017 |
| JP | 2017510307 A | 4/2017 |
| JP | 2022128381 A | 9/2022 |
| KR | 101274641 B1 | 6/2013 |
| KR | 20140133419 A | 11/2014 |
| WO | 1997033513 | 9/1997 |
| WO | 02064019 A2 | 8/2002 |
| WO | 2004016204 | 2/2004 |
| WO | 2004091419 | 10/2004 |
| WO | 2005120203 | 12/2005 |
| WO | 2006089069 | 8/2006 |
| WO | 2006105098 | 10/2006 |
| WO | 2006108065 A2 | 10/2006 |
| WO | 2006113394 A2 | 10/2006 |
| WO | 2008032316 A2 | 3/2008 |
| WO | 2008035089 | 3/2008 |
| WO | 2008103181 A1 | 8/2008 |
| WO | 2008152549 | 12/2008 |
| WO | 2009145633 | 12/2009 |
| WO | 2009148847 | 12/2009 |
| WO | 2010111678 A2 | 9/2010 |
| WO | 2012006066 A1 | 1/2012 |
| WO | 2012061825 | 5/2012 |
| WO | 2012095784 A1 | 7/2012 |
| WO | 2012103549 A1 | 8/2012 |
| WO | 2013022890 A1 | 2/2013 |
| WO | 2013044117 A1 | 3/2013 |
| WO | 2013044127 A1 | 3/2013 |
| WO | 2013044157 A1 | 3/2013 |
| WO | 2013044160 | 3/2013 |
| WO | 2013044165 A2 | 3/2013 |
| WO | 2013044174 A2 | 3/2013 |
| WO | 2014144107 | 3/2014 |
| WO | 2014053956 | 4/2014 |
| WO | 2014100795 | 6/2014 |
| WO | 2014209916 | 6/2014 |
| WO | 2014144070 | 9/2014 |
| WO | 2014144707 A1 | 9/2014 |
| WO | 2015021807 A1 | 2/2015 |
| WO | 2015038979 A1 | 3/2015 |
| WO | 2015200704 | 6/2015 |
| WO | 2015200718 | 6/2015 |
| WO | 2015200720 | 6/2015 |
| WO | 2015200722 | 6/2015 |
| WO | 2015200723 | 6/2015 |
| WO | 2015188867 A1 | 12/2015 |
| WO | 2015200707 A1 | 12/2015 |
| WO | 2016044651 A1 | 3/2016 |
| WO | 2016065205 A1 | 4/2016 |
| WO | 2016174612 | 11/2016 |
| WO | 2016180653 | 11/2016 |
| WO | 2016180654 | 11/2016 |
| WO | 2017152153 A1 | 9/2017 |
| WO | 2017165717 | 9/2017 |
| WO | 2018119360 A1 | 6/2018 |

OTHER PUBLICATIONS

PCT International Search Report and Written Opinion dated Jul. 7, 2014, for PCT/US2014/028381.

PCT International Search Report and Written Opinion dated Oct. 15, 2014, for PCT/US2014/043736.

PCT International Search Report and Written Opinion dated Feb. 1, 2016, for PCT/US2015/050789.

PCT International Search Report and Written Opinion dated Aug. 2, 2017, for PCT/US2017/023916.

European Partial Search Report dated Mar. 17, 2017, for 14762650.1.

European Partial Search Report dated Jun. 13, 2017, for 14817352.9.

European Partial Search Report dated Oct. 16, 2018 for 15842678.3.

European Extended Search Report dated Nov. 12, 2018, for Application No. 15812631.8.

European Extended Search Report dated Feb. 5, 2019 for 15842678.3.

Arami, Arash et al., "Instrumented Prosthesis for Knee Implant Monitoring", 2011 IEEE International Conference on Automation Science and Engineering, Trieste, Italy, Aug. 24-27, 2011, pp. 828-835.

Arami, Arash et al., "Accurate Measurement of Concurrent Flexion-Extension and Internal-External Rotations in Smart Knee Prostheses", IEEE Transactions on BioMedical Engineering, v. 60, No. 9, Sep. 2013, pp. 2504-2510.

Bosch Sensortec Data Sheet for BMI160 Small, low power inertial measurement unit, Doc Rev 0.8, Release Date Feb. 10, 2015, No. BST-BMI160-DS000-07, 110 pp.

Bosch for BMI160 Small, low power inertial measurement unit, Jan. 15, 2015, , 2 pp.

Bosch Press Release, "Bosch Sensortec launches first IMU with sub 1mA current consumption", Jun. 25, 2014, 3 pp.

Ebrahim, A. F., et al., "The use of fiber Bragg grating sensors in biomechanics and rehabilitation applications: The state-of-the-art and ongoing research topics", Sensors, 2012, v 12, No. 10, pp. 12890-12929.

Forchelet, David et al. "Enclosed Electronic System for Force Measurements in Knee Implants", Sensors 2014, vol. 14, pp. 15009-15021.

Graichen, F., et al., "Hip endoprosthesis for in vivo measurement of joint force and termperative", Journal of Biomechanics, 1999, v 32, No. 10, pp. 1113-1117.

Heinlein, Bernd et al., "Design, calibration and pre-clinical testing of an instrumented tibial tray", Journal of Biomechanics, vol. 40, 2007, pp. S4-S10.

Jacq, Caroline et al., "Investigation of Polymer Thick-Film Piezoresistors for Medical Wrists Rehabilitation and Artificial Knee Load Sensors", Procedia Engineering, vol. 87, 2014, pp. 1194-1197.

Kroft, Steve, "The Data Brokers: Selling your Personal Information" pp. 1-8, extracted from Google on Sep. 4, 2014 is a script from "The Data Brokers" aired on Mar. 9, 2014 on 60 Minutes CBS.

Simoncini, Matteo; "Design and integration of an instrumented knee prosthesis", Thesis No. 6379 (2014), École Polytechnique Fédérale de Lausanne.

Park, Min-Ho, MD et al., "Using a Tibial Short Extension Stem Reduces Tibial Component Loosening After Primary Total Knee Arthroplasty in Severely Varus Knees: Long-term Survival Analysis with Propensity Score Matching," The Journal of Arthroplasty, vol. 33, 2018, pp. 2512-2517.

U.S. Appl. No. 14/392,173, now abandoned (Patent Application Pub. No. 2016/0192878, cited herein).

(56) References Cited

OTHER PUBLICATIONS

Ries, Michael D., "Endosteal Referencing in Revision Total Knee Arthroplasty," The Journal of Arthroplasty, vol. 13, No. 1, pp. 85-91. (1998).
Almouahed S., et al., "New Trends in Instrumented Knee Prostheses," International Conference on Information and Communication Technologies: From Theory to Applications, Apr. 7-11, 2008, 6 Pages.
Angers-Goulet M., et al., "Up to Seven Years' Follow-up of Short Cemented Stems in Complex Primary Total Knee Arthroplasty: a Prospective Study," The Knee, Accepted on May 13, 2017, vol. 24, pp. 1166-1174.
Chandrakasan A.P., et al., "Next Generation Micro-Power Systems," Symposium on VLSI Circuits Digest of Technical Papers, 2008, pp. 1-5, 04 pages.
Christian R., MD., et al., "Short-keeled Cemented Tibial Components Show an Increased Risk for Aseptic Loosening," Clinical Orthopaedics and Related Research, Mar. 2013, vol. 471, No. 3, pp. 1008-1013.
D'Apuzzo M.R., et al., "Morbid Obesity Independently Impacts Complications, Mortality, and Resource Use After TKA," Clinical Orthopaedics and Related Research, Jan. 2015, Published Online on May 13, 2014, vol. 473, No. 01, pp. 57-63.
Extended European Search Report for European Application No. 14762269.0, mailed Oct. 24, 2016, 08 Pages.
Extended European Search Report for European Application No. 14762650.1, mailed Jul. 21, 2017, 10 Pages.
Extended European Search Report for European Application No. 17771204.9, mailed Feb. 28, 2020, 09 Pages.
Extended European Search Report for European Application No. 20214094.3, mailed May 28, 2021, 07 Pages.
Extended European Search Report for European Application No. 22153300.3, mailed Jul. 18, 2022, 07 Pages.
International Preliminary Report on Patentability for International Application No. PCT/US2014/028381, mailed Sep. 24, 2015, 13 Pages.
International Preliminary Report on Patentability for International Application No. PCT/US2014/043736, mailed Jan. 7, 2016, 11 Pages.
International Preliminary Report on Patentability for International Application No. PCT/US2015/050789, mailed Mar. 30, 2017, 07 Pages.
International Preliminary Report on Patentability for International Application No. PCT/US2017/023916, mailed Oct. 4, 2018, 20 Pages.
International Preliminary Report on Patentability for International Application No. PCT/US2020/036516, mailed Dec. 16, 2021, 10 Pages.
Loh N.C., et al., "Sub-10 cm3 Interferometric Accelerometer with Nano-g Resolution," Journal of Microelectromechanical Systems, vol. 11, No. 3, Jun. 2002, pp. 182-187.
Malin A.S., MD., et al., "Routine Surveillance of Modular PFC TKA Shows Increasing Failures after 10 Years," Clinical Orthopaedics and Related Research, Sep. 2010, vol. 468, No. 9, pp. 2469-2476.
Old A.B., et al., "Revision of Total Knee Arthroplasties Performed in Young, Active Patients with Posttraumatic Arthritis and Osteoarthritis," J. Knee Surg, Nov. 2017, vol. 30, No. 9, pp. 905-908, 1 Page.
Parratte S., MD., et al., "Do Stemmed Tibial Components in Total Knee Arthroplasty Improve Outcomes in Patients with Obesity?," Clinical Orthopaedics and Related Research, Jan. 2017, vol. 475, No. 1, pp. 137-145.
Partial Supplementary European Search Report for European Application No. 14762650.1, mailed Apr. 13, 2017, 08 Pages.
Partial Supplementary European Search Report for European Application No. 14817352.9, mailed Feb. 14, 2017, 09 Pages.
Patil S., MD., et al., "How Do Knee Implants Perform Past the Second Decade? Nineteen- to 25-year Followup of he Press-fit Condylar Design TKA," Clinical Orthopaedics and Related Research, Jan. 2015, vol. 473, No. 1, pp. 135-140.
Polla D.L., et al., "Microdevices in Medicine," Annual Review of Biomedical Engineering, 2000, vol. 02, pp. 551-576.
Singh U.K., et al., "Piezoelectric Power Scavenging of Mechanical Vibration Energy," Australian Mining Technology Conference, Oct. 2-4, 2007, pp. 111-118.
Xiang X., et al., "A Review of the Implantable Electronic Devices in Biology and Medicine," China Academic Journal Electronic Publishing House, vol. 32 (3), Mar. 3, 2004, pp. 462-467.
Yeh R., et al., "Single Mask, Large Force, and Large Displacement Electrostatic Linear Inchworm Motors," Journal of Microelectromechanical Systems, Aug. 4, 2002, vol. 11, No. 4, pp. 330-336, XP011064780.
Yiming L., et al., "Application of Wireless Sensor Networks in Healthcare," Chinese Journal of Medical Instrumentation, vol. 37, No. 5, Dec. 31, 2013, pp. 351-354 and Figure 1.
Yoon C., MD., et al., "Medial Tibial Periprosthetic Bone Resorption and Its Effect on Clinical Outcomes after Total Knee Arthroplasty: Cobalt-Chromium versus Titanium Implants," The Journal of Arthroplasty, Accepted Manuscript on Apr. 16, 2018, 43 Pages.
Yun K-S., et al., "A Surface-Tension Driven Micropump for Low-voltage and Low-Power Operations", Journal of Microelectromechanical Systems, Oct. 5, 2002, vol. 11, No. 5, pp. 454-461, DOI:10.1109/JMEMS.2002.803286, XP001192816.
Zimmer: "Persona the Personalized Knee Systems," Brochure, 2014, 12 Pages.
Laqua D., "Intelligent Power Management Enables Autonomous Power Supply of Sensor Systems for Modern Prostheses", Journal of Biomedical Engineering / Biomedizinische Technik, Published by Walter de Gruyter, Sep. 6, 2012, vol. 57, Supp. 1, pp. 247-250.
European Search Report in European Patent Application No. 23177756.6, dated Nov. 8, 2023, 8 Pages.

* cited by examiner

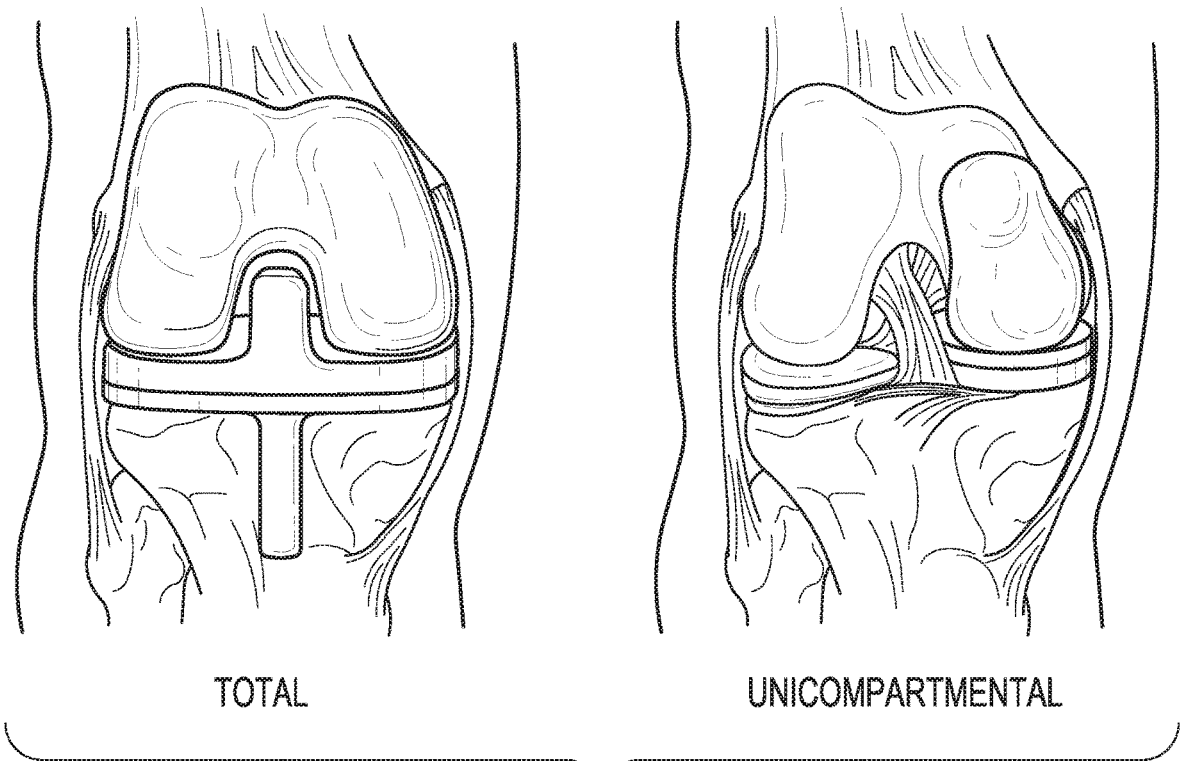
TOTAL UNICOMPARTMENTAL
Fig. 1
Fig. 2
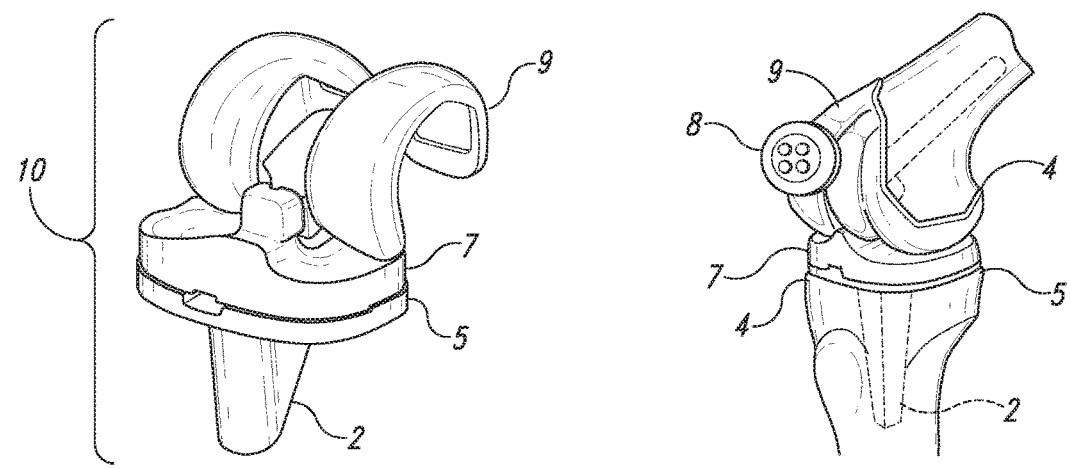

DEVICES, SYSTEMS AND METHODS FOR MONITORING KNEE REPLACEMENTS

CROSS-REFERENCE TO RELATED APPLICATION

This application is a continuation of U.S. patent application Ser. No. 14/392,173, filed Dec. 23, 2015, which is a national phase application under 35 U.S.C. § 371 of International Application No. PCT/US2014/043736, filed Jun. 23, 2014, which application claims the benefit under 35 U.S.C. § 119(e) of U.S. Provisional Patent Application No. 61/838,317 filed Jun. 23, 2013, which applications are incorporated herein by reference in their entireties for all purposes.

FIELD OF THE INVENTION

The present invention relates generally to knee replacements, and more specifically, to devices and methods for monitoring the performance of total and partial knee replacements

BACKGROUND

Description of the Related Art

Knee replacement is one of the most common reconstructive orthopedic surgical procedures. It may be carried out when the patient loses sufficient use of the knee, typically as a result of osteoarthritis, rheumatoid arthritis and other forms of arthritis (lupus, psoriatic and others), a previous knee injury (knee ligament tears (anterior cruciate, posterior cruciate, medial collateral and/or lateral collateral ligaments) and meniscus tears) and the sequellae of previous reconstructive surgery for the treatment for these conditions, articular cartilage injuries, joint dislocations, intra-articular fractures, and infections. Typically, the surgery is indicated for the treatment of extreme or constant joint pain, loss of range of motion, impaired ambulation and/or the loss of function and impairment in the activities of normal daily living; usually being indicated when there is evidence of significant loss or degeneration of the articular cartilage of all or parts of the knee.

The knee is generally divided into three "compartments", medial (the joint surface on the inside of the knee), lateral (the joint surface on outside of the knee), and patellofemoral (the joint between the kneecap and the thighbone or femur). Knee replacement can take a variety of different forms, depending on the degree of injury and/or the extent of the disease. In total knee replacement (TKR), both surfaces of the knee joint are replaced (i.e., the femoral articular surface and the tibial articular surface of the joint are replaced by a prosthesis); the patellar (kneecap) surface may/or may not be replaced depending on the degree of damage to the patella. In a partial or unicompartmental knee replacement, only one or two of the medial, lateral or patellofemoral portions of the joint are replaced (medial compartment replacement is the most common).

The various components of a TKR typically include femoral implant and a tibial implant (with or without replacing the surface of the patella). The femoral component consists of a rounded femoral condyle (often metal, but can be ceramic), the tibial component consists of a flat metal shell (with or without a stem that extends into the medullary canal of the tibia) that attaches to the tibia with an inner polymeric (often polyethylene, but ceramic and metal can be used) surface liner, and the patellar component (if present) consists of a polymeric "button" cemented to the posterior surface of the patella. Currently, the various components of a TKR can be made from a variety of different materials, including for example, polyethylene, ultrahigh molecular weight polyethylene, ceramic, surgical-grade stainless steel, cobalt chromium, titanium, and various ceramic materials. Within certain devices, the femoral implant (typically made of a metal such as stainless steel, titanium, or cobalt chromium) and the metal portion of the tibial component (typically also made of a metal such as stainless steel, titanium, or cobalt chromium) can be designed with a surface coating to encourage incorporation of the implant within the bone of the femur and the tibia. The prosthesis may or may not be held in place with the use of bone cement (PMMA—polymethylmethacrylate). Representative examples of the various components of a knee replacement are described in U.S. Pat. Nos. 5,413,604, 5,906,643, 6,019,794 and 7,922,771.

FIG. 1 shows a total knee joint of a type known in the art, as well as a unicompartmental (medial compartment) knee replacement. FIG. 2 illustrates the components and materials of a typical artificial joint (10), including a metallic tibial plate (5) and tibial stem (2) (present in this Figure, although some tibial plate components do not have stems), a polyethylene articulating surface (7), cement used to hold the various components in place (4), patellar "button" prosthesis (8), and the femoral knee component 9. FIG. 3 depicts another typical TKR, with a femoral component, a tibial plate and a patellar button which may be attached with screws and/or cement to the underlying bone (as opposed to a stemmed tibial plate).

Unfortunately, when a total knee is inserted, various complications may arise intra-operatively, in the post-operative period and over time. For example, intra-operatively, the surgeon may wish to confirm correct anatomical alignment of the prosthesis and/or any motion between the prosthesis and the surrounding bone so that adjustments can be made during the procedure. Post-operatively, the patient may experience inflammation and pain if there is slight movement, partial (subluxation) or full dislocation of any of the components of the knee prosthesis. Longer term, there may be progressive wear between the femoral surface and the tibial surface, which leads to improper operation of the knee joint. Depending on the types of materials used for the tibial surface and the femoral surface, prolonged wear can result in the generation of small debris particles which lead to inflammation and bone erosion surrounding the implant. A related common complication occurs when, over a period of time (for example 8-12 years), bone loss occurs in the tissues surrounding the implant (due to a process known as osteolysis) that leads to loosening and ultimately failure of the prosthesis. All of the above acute and chronic complications may degrade the performance of the knee, result in difficulty in movement and ambulation, and may cause pain and inflammation for the patient.

As mentioned, one of the most common and serious complications of TKR is erosion of the bone around the implant (osteolysis) which may be caused by material debris (metal, ceramic, and/or polyurethane fragments) generated by friction, and causing inflammation and bone loss. Other potential causes of inflammation and osteolysis are implant vibration and motion, improper patient usage/activities, improper alignment (including improper tracking of the patella), subclinical dislocation (subluxation) of the tibial-femoral joint and the patellar-femoral joint, mechanical wear and tear, material failure or breakage, loosening of the bond between the bone and the cement, lack of biocompatibility between the implant materials and the surrounding bone, metal allergy, and lack of biocompatibility between the bone cement and the surrounding bone. The ability to detect these changes early and institute corrective or preventative measures would be of great utility in the management of TKR patients. Additional complications that could benefit from early detection and intervention include infection, bone fracture, implant microfracture, nerve impingement, deep vein thrombosis, loss of motion, and instability.

Currently, post-operative, in-hospital monitoring of knee replacement surgery patients is conducted through personal visits by the hospital staff and medical team, physical examination of the patient, medical monitoring (vital signs, etc.), evaluation of knee range of motion (ROM), physiotherapy (including early mobilization and activity), and diagnostic imaging studies and blood work as required. Once the patient is discharged from hospital, prosthesis performance and patient satisfaction is checked during periodic doctor's office visits where a thorough history, physical exam and supplemental imaging and diagnostic studies are used to monitor patient progress and identify the development of any potential complications. During such visits, the surgeon typically evaluates the range of motion of the knee, attempts to identify any pain that occurs during certain motions or actions, and questions the patient to determine activity levels, daily functioning, pain control, and rehabilitation progress.

Unfortunately, most of the patient's recuperative period occurs between hospital and/or office visits. It can, therefore, be very difficult to accurately measure and follow full joint range of motion (ROM can change depending on pain control, degree of anti-inflammatory medication, time of day, recent activities, and/or how the patient is feeling at the time of the examination), "real life" prosthesis performance, patient activity levels, exercise tolerance, and the effectiveness of rehabilitation efforts (physiotherapy, medications, etc.) from the day of surgery through to full recovery. For much of this information, the physician is dependent upon patient self-reporting or third party observation to obtain insight into post-operative treatment effectiveness and recovery and rehabilitation progress; in many cases this is further complicated by a patient who is uncertain what to look for, has no knowledge of what "normal/expected" post-operative recovery should be, is non-compliant, or is unable to effectively communicate their symptoms. Furthermore, identifying and tracking complications (in and out of hospital) prior to them becoming symptomatic, arising between doctor visits, or those whose presence is difficult for the patient (and/or the physician) to detect would also provide beneficial, additional information to the management of TKR and partial knee replacement patients. Currently, in all instances, neither the physician nor the patient has access to the type of "real time," continuous, objective, prosthesis performance measurements that they might otherwise like to have.

The present invention discloses novel total and partial knee replacements which overcome many of the difficulties of previous knee prostheses, methods for constructing and monitoring these novel knee replacements, and further provides other related advantages.

SUMMARY

Briefly stated, full and partial knee prostheses are provided with a number of sensors to monitor the integrity and efficaciousness of the artificial knee joint within the patient. The sensors may be positioned on the outer surface of the prosthetic knee, on the inner surfaces of the prosthetic knee, within the prosthetic material (stainless steel, titanium, cobalt chromium, polyurethane, high molecular weight polyurethane, ceramics, etc.) itself, between the various components that comprise the prosthetic knee, the screws and/or fastening hardware (if present) used to secure the prosthesis in place, within the bone cement (e.g., PMMA, or PMMA and MMA copolymer blends) used to secure the knee (if present), and/or within the tissues surrounding the prosthesis. Within certain embodiments, the sensors are of the type that are passive and thus do not require their own power supply.

Within one aspect of the invention, assemblies are provided for positioning and placement within a patient an implant comprising a total or partial knee prosthesis; and one or more sensors positioned on, in, or around the prosthesis, and/or within the bone cement and/or bone screws or anchors utilized to attach the prosthesis. Within other aspects of the invention, medical devices are provided comprising at least one of: a tibial component, patellar prosthesis, or femoral component, and one or more sensors. For purpose of clarity, the one or more sensors may be purposely placed at specific locations on the knee replacement prosthesis, medical device, and/or bone screw or anchor, and/or randomly dispersed across, upon and within the knee replacement prosthesis, medical device, bone screw or anchor, and bone cement. Hence, use of the terms or phrases "are placed", "appear" or "utilized" should not be deemed to require specific placement, unless a specific placement is required.

Within various embodiments the sensor can be positioned on an outer surface of the prosthetic knee, on an inner surface of the prosthetic knee, within the materials used to construct the prosthetic knee, between the various components that make up the prosthetic knee, the screws and/or fastening hardware (if present) used to secure the prosthesis in place, on or in the bone cement used to secure the prosthetic knee, on or in the tissues surrounding the prosthetic knee (typically bone or bone marrow, but also muscle, ligament, tendon, joint capsule and/or synovial compartment), or any combination of these. Representative examples of sensors suitable for use within the present invention include accelerometers (acceleration, tilt, vibration, shock and rotation sensors), pressure sensors, contact sensors, position sensors, chemical microsensors, tissue metabolic sensors, mechanical stress sensors and temperature sensors. Within particularly preferred embodiments the sensor is a wireless sensor, or a sensor connected to a wireless microprocessor.

Within further embodiments a plurality of the aforementioned sensors are positioned on, within, or around (bone cement, bone screws or tissue) the prosthetic knee, and within preferred embodiments, the prosthetic knee can contain more than one type of sensor (e.g., one or more of, or any combination of the following: acceleration sensors, tilt sensors, vibration sensors, shock sensors, rotation sensors, pressure sensors, contact sensors, position sensors, chemical microsensors, tissue metabolic sensors, and mechanical stress sensors).

According to various embodiments, sensors are placed at different locations in a replacement knee joint in order to monitor the operation, movement, medical imaging (both prosthesis and surrounding tissues), function, wear, performance, potential side effects, medical status of the patient and the medical status of the artificial knee and its interface with the live tissue of the patient. Live, continuous, in situ, monitoring of patient activity, patient function, prosthesis activity, prosthesis function, prosthesis performance, prosthesis and joint alignment, patellar tracking, prosthesis and joint forces and mechanical stresses, prosthesis and surrounding tissue anatomy (imaging), mechanical and physical integrity of the prosthesis, patellar tracking and potential side effects is provided. In addition, information is available on many aspects of the knee replacement prosthesis and its interaction with the patient's own body tissues, including clinically important measurements not currently available through physical examination, medical imaging and diagnostic medical studies.

According to one embodiment, the sensors provide evaluation data on the range of motion (ROM) of the knee. Currently, ROM is usually measured clinically by the physician passively moving the knee joint through a full range of motion during physical examination and recording the results (degrees of flexion, extension, anterior/posterior stability and medial/lateral stability; see, e.g., FIG. 4). Motion sensors and accelerometers can be used to accurately determine the full ROM of the prosthetic knee joint both during physical examination and during normal daily activities between visits. Similarly, motion sensors and accelerometers can be used to accurately measure any anterior/posterior or medial/lateral instability (including full, partial or subclinical dislocation) of the prosthetic knee joint both during physical examination and during normal daily activities between visits. Additionally, motion sensors and accelerometers can be used to accurately measure any improper tracking of the patella and/or patellar instability (including full, partial or subclinical subluxation) during physical examination and during normal daily activities between visits.

According to one embodiment, contact sensors are provided between the prosthesis and the surrounding bone, between the screws and/or fastening hardware (if present) and the surrounding bone, between the prosthesis and the surrounding bone cement (if present), and/or between the bone cement (if present) and the surrounding bone in order to measure bone erosion and loosening around the implant. In other embodiments, vibration sensors are provided to detect the vibration between the prosthesis and the surrounding bone, between the screws and/or fastening hardware (if present) and the surrounding bone, between the prosthesis and the surrounding bone cement, between the bone cement and the surrounding bone as an early indicator of motion and loosening. In other embodiments, strain gauges are provided to detect the strain between the prosthesis and the surrounding bone, between the screws and/or fastening hardware (if present) and the surrounding bone, between the prosthesis and the surrounding bone cement, between the bone cement and the surrounding bone, and also the strain which is exerted on the various portions of the prosthesis. Sudden increases in strain may indicate that too much stress is being placed on the replacement prosthesis, which may increase damage to the body. For example, a gradual, long-term decrease in strain may cause bone reabsorption around the implant, leading to loosening of the prosthesis or fractures in the bone surrounding the prosthesis, while a gradual, long-term increase in strain may lead to microfractures of the prosthesis materials themselves.

According to other embodiments, accelerometers are provided which detect vibration, shock, tilt and rotation. According to other embodiments, sensors for measuring surface wear, such as contact or pressure sensors, may be embedded at different depths within the femoral articular surface, the tibial articular surface, and/or the patellar articular surface in order to monitor articular surface erosion. In other embodiments, position sensors, as well as other types of sensors, are provided which indicate the range of motion and monitor for partial (or complete) femoral-tibial knee dislocation or subluxation in actual use over a period of time, improper tracking of the patella and/or subluxation of the patellar-femoral joint, or movement between the interconnected components of the prosthesis (and the anchoring hardware) itself.

Within further embodiments, the artificial knee (total or partial) can contain sensors at specified densities in specific locations. For example, the artificial knee can have a density of sensors of greater than one, two, three, four, five, six, seven, eight, nine, or ten sensors (e.g., acceleration sensors, tilt sensors, vibration sensors, shock sensors, rotation sensors, pressure sensors, contact sensors, position sensors, chemical microsensors, tissue metabolic sensors, and mechanical stress sensors, or any combination of these) per square centimeter of the device. Within other embodiments, the artificial knee (total or partial) can have a density of sensors of greater than one, two, three, four, five, six, seven, eight, nine, or ten sensors (e.g., acceleration sensors, tilt sensors, vibration sensors, shock sensors, rotation sensors, pressure sensors, contact sensors, position sensors, chemical microsensors, tissue metabolic sensors, and mechanical stress sensors, or any combination of these) per cubic centimeter of the device. Within related embodiments, the sensors (e.g., acceleration sensors, tilt sensors, vibration sensors, shock sensors, rotation sensors, pressure sensors, contact sensors, position sensors, chemical microsensors, tissue metabolic sensors, and mechanical stress sensors) can be positioned at particular locations on, within, or around the artificial knee, including for example, the femoral component (medial, lateral or both), the tibial plate, the tibial stem (if present), the tibial lining, the prosthetic patellar lining, within portions of the device which are to be connected (e.g., the connecting segments of the tibial cup and the tibial lining), the screws and/or fastening hardware (if present) used to secure the prosthesis in place, and around the artificial knee (on or in the bone cement used to secure the prosthetic knee, on or in the tissues surrounding the prosthetic knee—typically bone or bone marrow, but also muscle, ligament, tendon, joint capsule and/or synovial compartment).

Within certain embodiments of the invention, the total or partial knee prosthesis is provided with a specific unique identifying number, and within further embodiments, each of the sensors on, in or around the prosthetic knee each have either a specific unique identification number, or a group identification number (e.g., an identification number that identifies the sensor as an acceleration sensor, a tilt sensor, a vibration sensor, a shock sensor, a rotation sensor, a pressure sensor, a contact sensor, a position sensor, a chemical microsensor, a tissue metabolic sensor, or a mechanical stress sensor). Within yet further embodiments, the specific unique identification number or group identification number is specifically associated with a position on, in or around the prosthetic knee.

Within other aspects of the invention methods are provided for monitoring an implanted total or partial knee prosthesis comprising the steps of transmitting a wireless electrical signal from a location outside the body to a location inside the body; receiving the signal at a sensor positioned on, in or around an artificial knee located inside the body; powering the sensor using the received signal; sensing data at the sensor; and outputting the sensed data from the sensor to a receiving unit located outside of the body.

Within other aspects of the invention methods are provided for imaging a knee replacement or medical device as provided herein, comprising the steps of (a) detecting the location of one or more sensors in a knee replacement or medical device; and (b) visually displaying the location of said one or more sensors, such that an image of the knee replacement or medical device is created. Within various embodiments, the step of detecting may be done over time, and the visual display may thus show positional movement over time. Within certain embodiments the image which is displayed is a two or three-dimensional image. Within preferred embodiments the various images may be collected and displayed in a time-sequence (e.g., as a moving image or 'movie-like' image).

The imaging techniques provided herein may be utilized for a wide variety of purposes. For example, within one aspect, the imaging techniques may be utilized during a surgical procedure in order to ensure proper placement and working of the knee replacement or medical device. Within other embodiment, the imaging techniques may be utilized post-operatively in order to examine the knee replacement or medical device, and/or to compare operation and/or movement of the device over time.

The integrity of the partial or total knee prosthesis can be wirelessly interrogated and the results reported on a regular basis. This permits the health of the patient to be checked on a regular basis or at any time as desired by the patient and/or physician. Furthermore, the prosthesis can be wirelessly interrogated when signaled by the patient to do so (via an external signaling/triggering device) as part of "event recording"—i.e. when the patient experiences a particular event (e.g. pain, injury, instability, etc.) she/he signals/triggers the device to obtain a simultaneous reading in order to allow the comparison of subjective/symptomatic data to objective/sensor data. Matching event recording data with sensor data can be used as part of an effort to better understand the underlying cause or specific triggers of a patient's particular symptoms. Hence, within various embodiments of the invention methods are provided for detecting and/or recording an event in a subject with one of the total or partial knee replacements provided herein, comprising the interrogating at a desired point in time Hence, within one aspect of the invention methods are provided for detecting and/or recording an event in a subject with a knee replacement or medical device as provided herein, comprising the step of interrogating at a desired point in time the activity of one or more sensors within the knee replacement or medical device, and recording said activity. Within various embodiments, they may be accomplished by the subject and/or by a health care professional. Within related embodiments, the step of recording may be performed with one or more wired devices, or, wireless devices that can be carried, or worn (e.g., a cellphone, watch, wristband, and/or glasses). Within further embodiments, the worn devices (e.g. cellphone, watch, wristband and/or glasses may have sufficient processing power and memory to be able to carry out further data collection and analysis.

Within further embodiments, each of the sensors contains a signal-receiving circuit and a signal output circuit. The signal-receiving circuit receives an interrogation signal that includes both power and data collection request components. Using the power from the interrogation signal, the sensor powers up the parts of the circuitry needed to conduct the sensing, carries out the sensing, and then outputs the data to the interrogation module. The interrogation module acts under control of a control unit which contains the appropriate I/O circuitry, memory, a controller in the form of a microprocessor, and other circuitry in order to drive the interrogation module. Within yet other embodiments the sensor (e.g., an acceleration sensor, a tilt sensor, a vibration sensor, a shock sensor, a rotation sensor, a pressure sensor, a contact sensor, a position sensor, a chemical microsensor, a tissue metabolic sensor, or a mechanical stress sensor) are constructed such that they may readily be incorporated into or otherwise mechanically attached to the knee prosthesis (e.g., by way of a an opening or other appendage that provides permanent attachment of the sensor to the knee prosthesis) and/or readily incorporated into the bone cement or the tissues that surround the knee prosthesis.

Within yet other aspects of the invention methods devices are provided suitable for transmitting a wireless electrical signal from a location outside the body to a location inside the body; receiving the signal at one of the aforementioned sensors positioned on, in or around a prosthetic knee located inside the body; powering the sensor using the received signal; sensing data at the sensor; and outputting the sensed data from the sensor to a receiving unit located outside of the body. Within certain embodiments the receiving unit can provide an analysis of the signal provided by the sensor.

The data collected by the sensors can be stored in a memory located within the femoral component, the tibial plate and/or the tibial stem. During a visit to the physician, the data can be downloaded via a wireless sensor, and the doctor is able to obtain data representative of real-time performance of the prosthesis.

The advantages obtained include more accurate monitoring of the prosthesis and permitting medical reporting of accurate, in situ, data that will contribute to the health of the patient. The details of one or more embodiments are set forth in the description below. Other features, objects and advantages will be apparent from the description, the drawings, and the claims. In addition, the disclosures of all patents and patent applications referenced herein are incorporated by reference in their entirety.

BRIEF DESCRIPTION OF THE DRAWINGS

FIG. 1 is an illustration of a total knee replacement, and a unicompartmental knee replacement.

FIG. 2 is an exploded view which illustrates various components of a total knee replacement.

DETAILED DESCRIPTION OF THE INVENTION

Figure 3:
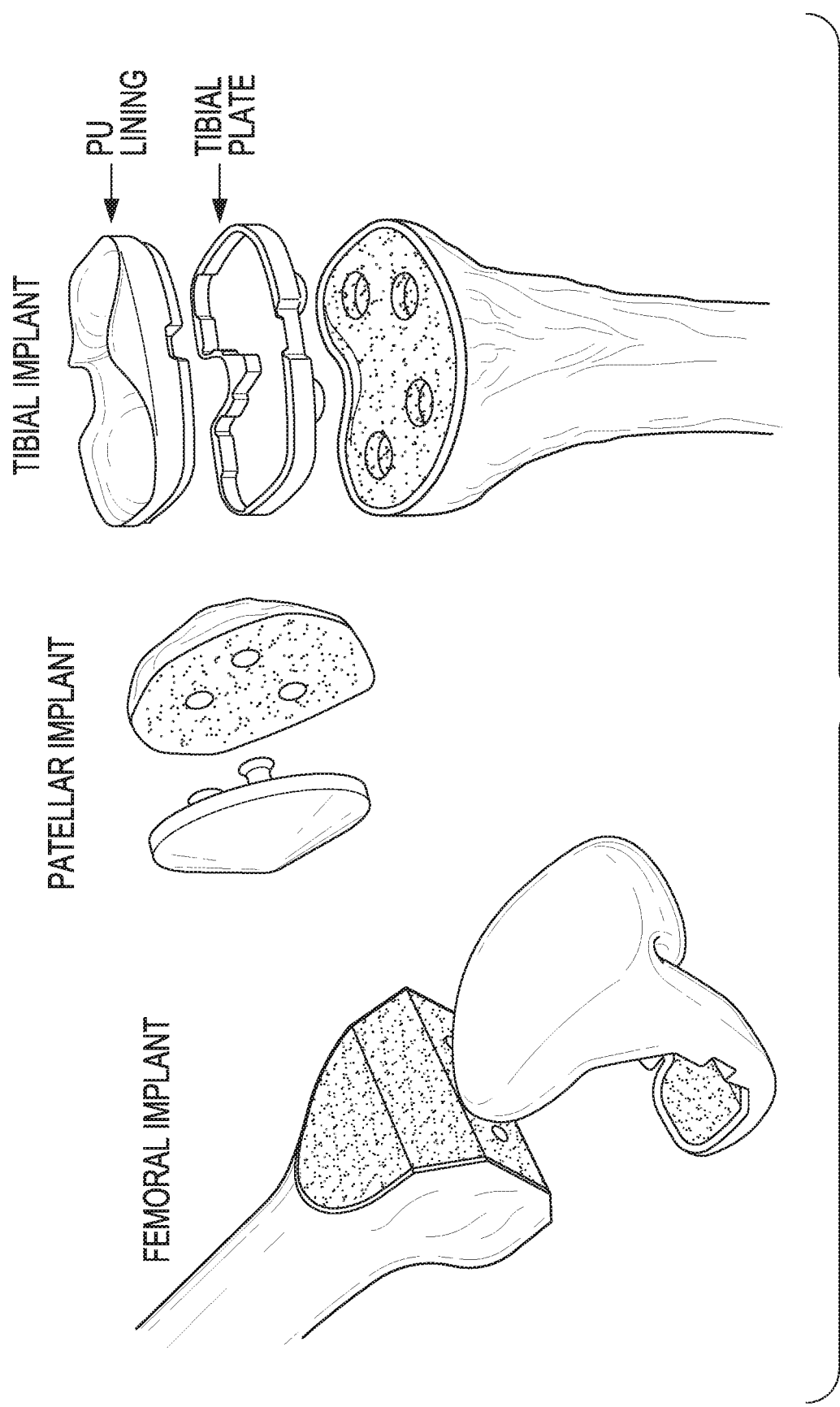
FIG. 3 illustrates the components of another total knee replacement.

Briefly stated the present invention provides a variety of knee replacements that can be utilized to monitor the integrity and efficaciousness of the device. Prior to setting forth the invention however, it may be helpful to an understanding thereof to first set forth definitions of certain terms that are used hereinafter.

"Knee replacement" or "knee prosthesis" as that term is utilized herein, may take a variety of different forms and may involve replacement of all (total knee replacement) or portions (partial knee replacement) of the patient's knee joint with synthetic materials. In total knee replacement (TKR), both the femoral side and the tibial side are replaced. In a partial or unicompartmental knee replacement, only one or two portions (surfaces—tibial or femoral; or compartments—medial, lateral or patellar) of the knee are replaced.

The various components of a TKR can typically include a femoral implant, a patellar implant, and a tibial implant (which can be composed of a tibial plate—with or without a stem—and a tibial liner). Currently, the various components can be made from a variety of different materials, including for example, polyethylene, ultrahigh molecular weight polyethylene, ceramic, surgical-grade stainless steel, cobalt chromium, titanium, and various ceramic materials. Within certain devices, the femoral implant (typically made of a metal such as stainless steel, titanium, or cobalt chromium) can be designed with a bone surface coating to encourage incorporation of the implant within the femur and the tibial plate (and stem) can also have a surface coating to encourage incorporation into the tibia. Representative examples of the various components of a knee replacement are described in U.S. Pat. Nos. 5,413,604, 5,906,643, 6,019,794 and 7,922,771.

"Bone Cement" refers to a material that can be administered between the prosthetic hardware and the surrounding bone and hardens in place when cooled (or otherwise activated); it is an agent used to secure one or more of the components (the prosthetic femur surface, the tibial plate/stem, the patellar "button") of the prosthesis to the appropriate bony tissue (femur, tibia, tibial medulla, patella). Bone cement is often composed of PMMA (polymethylmethacrylate) or PMMA and MMA copolymer blends. It should be noted that bone screws and/or other metallic (or polymeric) securing devices can also be used to assist in anchoring the prosthetic components to the surrounding bony tissues.

The present invention provides knee prosthesis (which may include a full or a partial implant), medical devices (e.g., a portion of a knee implant, and/or components or materials which are useful in the process of implanting the device), and kits (e.g., a knee prosthesis, medical device, and additional necessary materials such as bone cement and any associated delivery devices), all of which have sensors as described in further detail below. The knee prosthesis, medical devices and kits as provided herein (including related materials such as bone cement) are preferably sterile, non-pyrogenic, and/or suitable for use and/or implantation into humans. However, within certain embodiments of the invention the knee prostheses, medical devices and/or kits can be made in a non-sterilized environment (or even customized to an individual subject), and sterilized at a later point in time.

"Sensor" refers to a device that can be utilized to measure one or more different aspects of a body, of a knee prosthesis, medical device or kit inserted within a body, and/or the integrity, impact, efficaciousness or effect of the knee prosthesis, medical device or kit inserted within a body. Representative examples of sensors suitable for use within the present invention include, for example, fluid pressure sensors, contact sensors, position sensors, pulse pressure sensors, liquid (e.g., blood) volume sensors, liquid (e.g., blood) flow sensors, chemistry sensors (e.g., for blood and/or other fluids), metabolic sensors (e.g., for blood and/or other fluids), accelerometers, mechanical stress sensors and temperature sensors. Within certain embodiments the sensor can be a wireless sensor, or, within other embodiments, a sensor connected to a wireless microprocessor. Within further embodiments one or more (including all) of the sensors can have a Unique Sensor Identification number ("USI") which specifically identifies the sensor.

A wide variety of sensors (also referred to as Microelectromechanical Systems or "MEMS", or Nanoelectromechanical Systems or "NEMS", and BioMEMS or BioNEMS, see generally https://en.wikipedia.org/wiki/MEMS) can be utilized within the present invention. Representative patents and patent applications include U.S. Pat. Nos. 7,383,071 and 8,634,928, and U.S. Publication Nos. 2010/0285082, and 2013/0215979. Representative publications include "Introduction to BioMEMS" by Albert Foch, CRC Press, 2013; "From MEMS to Bio-MEMS and Bio-NEMS: Manufacturing Techniques and Applications by Marc J. Madou, CRC Press 2011; "Bio-MEMS: Science and Engineering Perspectives, by Simona Badilescu, CRC Press 2011; "Fundamentals of BioMEMS and Medical Microdevices" by Steven S. Saliterman, SPIE—The International Society of Optical Engineering, 2006; "Bio-MEMS: Technologies and Applications", edited by Wanjun Wang and Steven A. Soper, CRC Press, 2012; and "Inertial MEMS: Principles and Practice" by Volker Kempe, Cambridge University Press, 2011; Polla, D. L., et al., "Microdevices in Medicine," Ann. Rev. Biomed. Eng. 2000, 02:551-576; Yun, K. S., et al., "A Surface-Tension Driven Micropump for Low-voltage and Low-Power Operations," *J. Microelectromechanical Sys.*, 11:5, October 2002, 454-461; Yeh, R., et al., "Single Mask, Large Force, and Large Displacement Electrostatic Linear Inchworm Motors," *J. Microelectromechanical Sys.*, 11:4, August 2002, 330-336; and Loh, N. C., et al., "Sub-10 cm$^3$ Interferometric Accelerometer with Nano-g Resolution," *J. Microelectromechanical Sys.*, 11:3, June 2002, 182-187; all of the above of which are incorporated by reference in their entirety.

Within various embodiments of the invention the sensors described herein may be placed at a variety of locations and in a variety of configurations, including on the inside, within, and/or outer surface (or surfaces) of the knee prosthesis, medical device or kit, as well as between the knee prosthesis, medical device or kit and any device it might carry (e.g., a delivery or installation device). As will be readily evident given the disclosure provided herein, the sensors may be placed at multiple locations (i.e., inside, within and on the outer surface) of the knee prosthesis, medical device or kit at the same time. Within certain embodiments the knee prosthesis, medical device or kit, associated medical device (e.g., delivery instrument) or kit comprises sensors at a density of greater than 1, 2, 3, 4, 5, 6, 7, 8, 9, 10 or greater than 10 sensors per square centimeter. Within other aspects the knee prosthesis, medical device or kit, associated medical device (e.g., delivery instrument) or kit comprises sensors at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter. Within various embodiments the at least one or more of the sensors may be placed randomly, or at one or more specific locations within the catheter, medical device, or kit as described herein.

In various embodiments, the sensors may be placed within specific locations and/or randomly throughout the knee prosthesis, medical device or kit, associated medical device (e.g., delivery instrument) or kit. In addition, the sensors may be placed in specific patterns (e.g., they may be arranged in the pattern of an X, as oval or concentric rings around the knee prosthesis, medical device or kit, associated medical device (e.g., delivery instrument) or kit.

Representative Embodiments of Knee Prosthesis, Medical Devices and Kits

In order to further understand the various aspects of the invention provided herein, the following sections are provided below: A. Knee Prosthesis, Medical Devices and Kits and their Use; B. Use of Knee Prosthesis, Medical Devices and Kits to Deliver Therapeutic Agent(s); C. Use of a Knee Prosthesis, Medical Device or Kit having Sensors to Measure Degradation or Wearing of an Implant; D. Methods for Monitoring Infection in Knee Prosthesis, Medical Devices and Kits; E. Further Uses of Sensor-containing Knee Prosthesis, Medical Devices and Kits in Healthcare; F. Generation of Power from Knee Prosthesis, Medical Devices and Kits; G. Medical Imaging and Self-Diagnosis of Assemblies Comprising Knee Prosthesis, Medical Devices and Kits, Predictive Analysis and Predictive Maintenance; H. Methods of Monitoring Assemblies Comprising Knee Prosthesis, Medical Devices and Kits; and I. Collection, Transmission, Analysis, and Distribution of Data from Assemblies Comprising Knee Prosthesis, Medical Devices and Kits.

A. Knee Prosthesis, Medical Devices and Kits and their Use

Knee replacement is carried out when the patient loses sufficient use of the knee so as to result in disability, loss of movement and function, impaired ambulation, and/or continuous joint pain and discomfort. Common causes of impaired knee function leading to total or partial knee replacement include various types of arthritis (such as rheumatoid arthritis or osteoarthritis, and trauma (for example, previous knee ligament injuries or cartilage/meniscus tears). In most patients, the operation is successful in improving ambulation, restoring normal daily function and reducing pain; as a result, it is a very common orthopedic procedure in the Western World.

FIGS. 5, 6, 7, 8 and 9 illustrate several prosthesis 10 in the form of a total knee replacement having one or more sensors positioned in or on the prosthesis in order to monitor, in situ, the real-time operation of the prosthesis, levels of patient function and activity, and the prosthesis performance acutely and over time. A variety of these sensors will now be described according to various embodiments.

Figure 5:
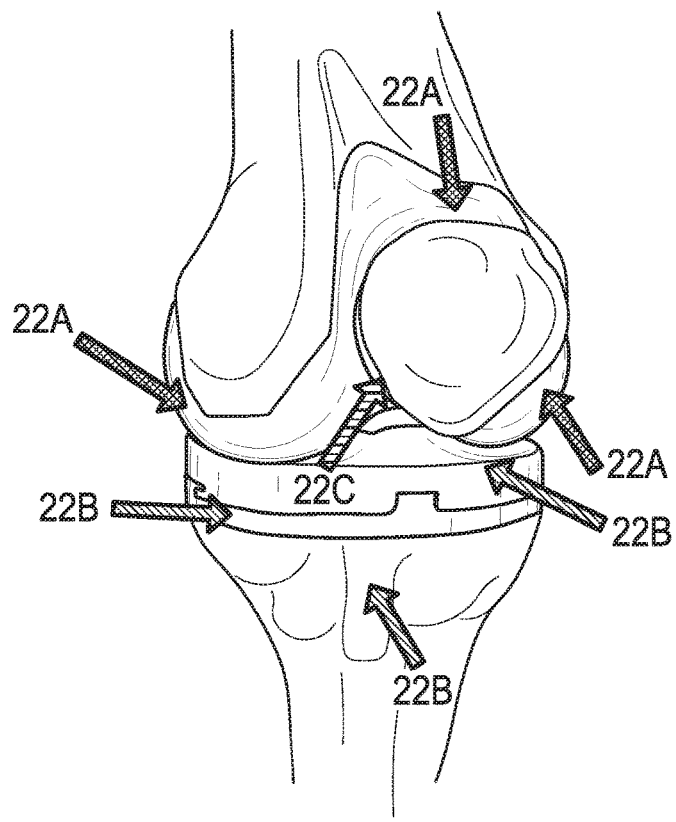
FIG. 5 illustrates a TKR with various contact sensors.

In one embodiment shown in FIG. 5, one or more contact sensors 22 are provided throughout the implant, including contact sensors 22A distributed on and within the femoral condyle prosthesis-bone interface, contact sensors 22B distributed on and within the tibial bone—metal plate (and stem if present) interface, and contact sensors 22C distributed on within the patellar prosthesis (patellar "button")—patellar bone interface. In some embodiments, the contact sensors are on the prosthetic components themselves (tibial, femur and patellar segments), while in others the contact sensors are contained on/within the bone cement (if present) used to secure the prosthesis to the surrounding bone, and in still other embodiments the contact sensors are contained on/within both the prosthetic components and the bone cement (PMMA).

In various embodiments, these sensors may be positioned in a variety of different patterns on the prosthetic components based on their contact locations with respect to the surrounding bone (femur, tibia and/or patella) and/or the surrounding bone cement (if present). For example, they may be arranged in the pattern of an X, as oval or concentric rings around the various components or in various other patterns, in order to collect accurate data on the physical contact between the tibial component and the tibia and/or surrounding bone cement (if present), the femoral component and the femur and/or surrounding bone cement (if present), and the patellar component and the patella and/or surrounding bone cement (if present). Contact sensors can also be dispersed within/arranged within the bone cement (if present) so as to collect data on the physical contact between the bone cement and the components of the prosthesis (femoral, tibial and patellar) and/or between the bone cement and the bone (femur, tibia, patella) itself.

Within various embodiments of the invention contact sensors are placed on the tibial component, femoral component, and/or patellar components of the knee prosthesis, and/or in the bone cement securing the components of the prosthesis to the surrounding bone, at a density of greater than one, two, three, four, five, six, seven, eight, nine, or ten sensors per square centimeter, or, per cubic centimeter of the prosthetic device component and/or per cubic centimeter of bone cement.

Within other aspects of the invention methods are provided for imaging a knee replacement or medical device as provided herein, comprising the steps of (a) detecting the location of one or more sensors in a knee replacement or medical device; and (b) visually displaying the location of said one or more sensors, such that an image of the knee replacement or medical device is created. Within various embodiments, the step of detecting may be done over time, and the visual display may thus show positional movement over time. Within certain preferred embodiments the image which is displayed is a three-dimensional image.

The imaging techniques provided herein may be utilized for a wide variety of purposes. For example, within one aspect, the imaging techniques may be utilized during a surgical procedure in order to ensure proper placement and working of the knee replacement or medical device. Within other embodiment, the imaging techniques may be utilized post-operatively in order to examine the knee replacement or medical device, and/or to compare operation and/or movement of the device over time.

Within one embodiment the contact sensors 22 (22A, 22B, 22C) can detect loosening of the prosthesis 10 and its connection to the surrounding cement (if present) and/or bone. For example, the contact sensors located on/in the tibial component and/or on/in the bone cement around the tibial component (22B), can detect loosening of the tibial component within the tibia; this can be detected acutely during surgery and alert the surgeon that some intra-operative adjustment is required. Progressive loosening of the tibial component within the tibia over time (as compared to post-operative levels) is a common complication that occurs when bone loss takes place (e.g., due to a process known as osteolysis); this too can be detected by the contact sensors on/in the tibial component and/or on/in the surrounding bone cement. Furthermore, contact sensors located between segments of the tibial component (e.g. between the tibial plate and the tibial liner) can detect abnormal movement, loosening, or wear between component segments; these sensors can be "matching" (i.e. "paired" between adjacent components) so as to also allow accurate fitting during (and after) surgical placement.

Thus, in the embodiment of FIG. 5, a variety of contact sensors are provided in order to monitor contact between the tibia and the tibial component, between the femur and the femoral component, between the patella and the patellar component, between the complimentary segments of the individual prosthetic components, and between the various articular surfaces present (medial and lateral tibial-femoral joint; the patellar-femoral joint) of a multi-compartmental or uni-compartmental prosthetic knee joint. Specifically, full or partial dislocation (subluxation) of the femoral prosthetic joint surface from the natural or synthetic tibial joint surface (medial, lateral or both) of a prosthetic knee is a common complication of knee replacement, often occurring shortly after surgery (particularly during the post-operative recovery period when the surrounding muscles and ligaments are still healing from surgery). Contact sensors on the femoral component articular surface and/or tibial component articular surface can alert the patient and the healthcare provider if joint dislocation or subluxation has occurred. This is of particular value in the detection of subclinical partial or incomplete dislocation (subluxation) of the knee joint which may not be readily evident to the patient or the physician; this is of greatest concern during early mobilization and post-operative rehabilitation efforts. Additionally, contact sensors on the various knee components can determine of the joint is functioning and aligning (tracking) correctly during movement and activity. This is particularly true with respect to the movement of the knee cap, as accurate patellar tracking can be difficult to accurately measure clinically; accurate measurement of patellar tracking, both intra-operatively and post-operatively, would be beneficial.

Figure 6:
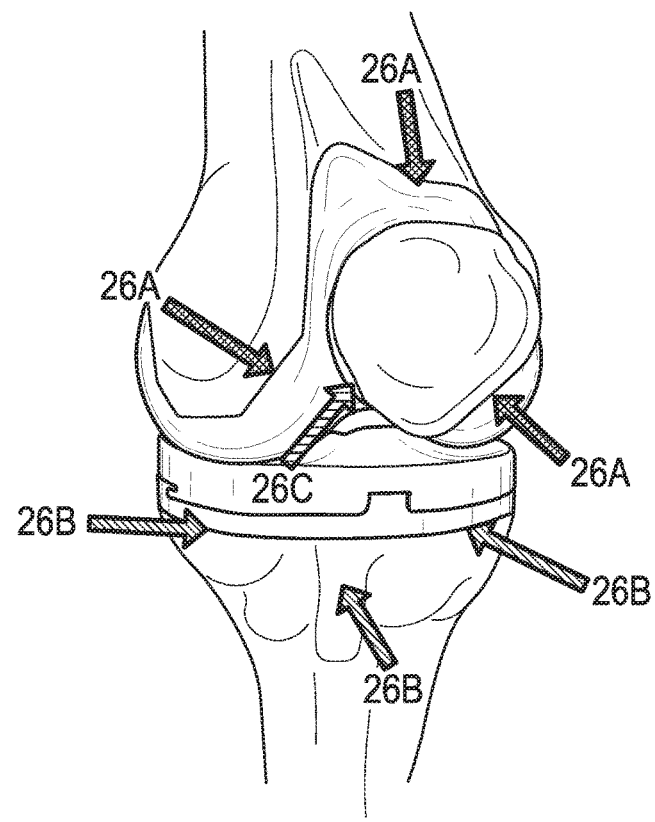
FIG. 6 illustrates a TKR with various strain gauges.

In another embodiment shown in FIG. 6, one or more strain gauges (or sensors) 26 are provided throughout the implant, including strain gauges 26A distributed on and within the femoral condyle prosthesis-bone interface, strain gauges 26B distributed on and within the tibial bone—metal plate (and stem if present) interface, and strain gauges 26C distributed on within the patellar prosthesis (patellar "button")—patellar bone interface. In some embodiments, the strain gauges are on the prosthetic components themselves (tibial, femur and patellar segments), while in others the strain gauges are contained on/within the bone cement (if present) used to secure the prosthesis to the surrounding bone, and in still other embodiments the strain gauges are contained on/within both the prosthetic components and the bone cement (PMMA).

In various embodiments, these strain gauges may be positioned in a variety of different patterns on the prosthetic components based on their contact locations with respect to the surrounding bone (femur, tibia and/or patella) and/or the surrounding bone cement (if present). For example, they may be arranged in the pattern of an X, as oval or concentric rings around the various components or in various other patterns, in order to collect accurate data on the physical strain experienced by the prosthetic components, the surrounding bone cement (if present), and the surrounding bone (femur, tibia, patella) tissue.

Within various embodiments of the invention strain sensors are placed on the tibial component, femoral component, patellar prosthesis, and/or in the bone cement at a density of greater than one, two, three, four, five, six, seven, eight, nine, or ten sensors per square centimeter of the prosthetic components, or, per cubic centimeter of PMMA bone cement.

The strain gauges 26 provide a different data point than the contact sensors 22. The contact sensors 22 merely specify whether there is current contact between adjacent structures and thus provide a good indication of whether there is abutting contact between two surfaces. However, they do not provide an indication of the physical strain that is present in either the prosthetic surfaces or the surrounding bone; on the other hand, the strain sensors 26 output data is indicative of the mechanical strain forces being applied across the implant which, if not corrected, can be a harbinger of future loosening and prosthesis failure. In addition, the strain gauges 26 may be of the type which indicates the strain which is being exhibited between two surfaces, such as between the tibial side and the bone, the femoral side and the bone, the patellar side and the bone, between the prosthetic components (tibial, femoral and patellar) and the bone cement, or between the tibial, femoral, and patellar components themselves.

As shown in FIG. 6, strain gauges 26 may be positioned at various locations on the tibial component to detect strain encountered between the tibial prosthesis and the surrounding tibial bone (and/or bone cement if present). Many tibial prostheses contain a stem that extends into the medullary canal of the tibia to enhance anchoring and stability. A decrease in strain in the tibial prosthesis and/or tibial bone cement may indicate that conditions are present that could potentially lead to bone resorbtion (loss) in all, or parts, of the tibial canal; bone resorbtion can lead to loosening of the prosthesis, or to tibial fracture (conversely, increased strain would favour bone growth in the region). Therefore, the strain sensors can provide an indication of the strain that is present in the tibial shaft and measure the most important mechanical strain forces being applied across the implant which, if mal-aligned or not corrected, have a high probability of resulting in loosening and prosthesis failure. An increase of strain may also indicate bone hypertrophy (growth), which can be a source of pain. The same dynamic exists in the interface between the femoral and patellar prosthetic components (and/or bone cement) and the femur and patellar; strain gauges 26 of the present invention can be used to monitor for these purposes as well. "Real life" strain information would not just be beneficial to the doctor and patient, who could use the data to determine the (positive and negative) effects of various activities on prosthetic-bone health, but also to manufacturers who could use it to design better prostheses.

Figure 7:
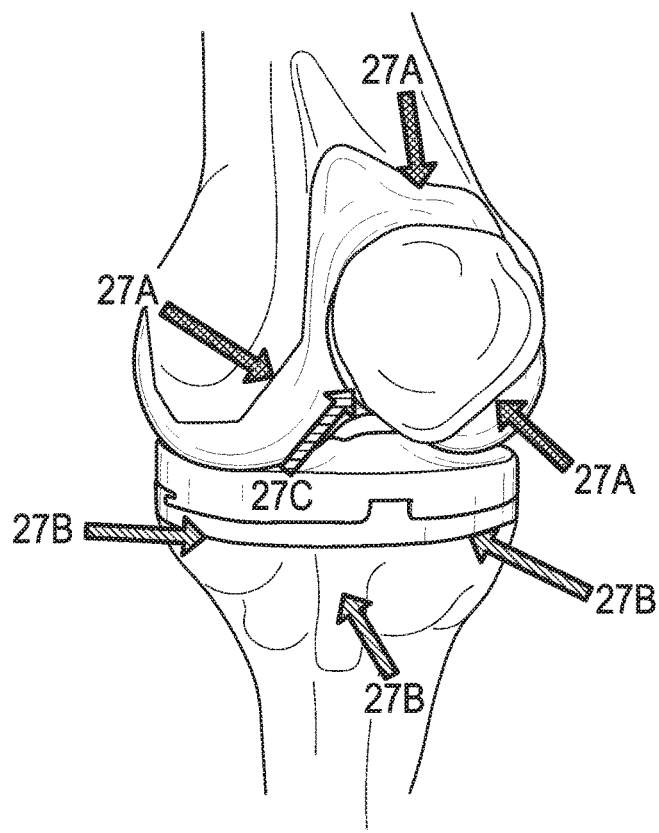
FIG. 7 illustrates a TKR with various accelerometers.

In another embodiment shown in FIG. 7, one or more accelerometers 27 are provided throughout the implant, including accelerometers 27A distributed on and within the femoral condyle prosthesis, accelerometers 26B distributed on and within the tibial plate (and stem if present) and tibial liner, and accelerometers 27C distributed on within the patellar prosthesis (patellar "button"). In some embodiments, the accelerometers are on/within the prosthetic components themselves (tibial, femur and patellar segments), while in others the accelerometers are contained on/within the bone cement (if present) used to secure the prosthesis to the surrounding bone, and in still other embodiments the accelerometers are contained on/within both the prosthetic components and the bone cement (PMMA).

In various embodiments, accelerometers may be positioned in a variety of different patterns within/on the prosthetic components based on their contact locations with respect to the surrounding bone (femur, tibia and/or patella), the surrounding bone cement (if present), the articular interface between the different prosthetic components (tibial-femoral joint and the patellar-femoral joint), and/or between sub-segments of a component (e.g. between the tibial plate and the tibial liner). For example, they may be arranged in the pattern of an X, as oval or concentric rings around, or within, the various components or in various other patterns, in order to collect accurate data experienced by the prosthetic components, the surrounding bone cement (if present), and (by extension) the surrounding bone (femur, tibia, patella) tissue.

Within various embodiments of the invention accelerometers are placed on/within the tibial component, femoral component, patellar prosthesis, and/or in the bone cement at a density of greater than one, two, three, four, five, six, seven, eight, nine, or ten sensors per square centimeter, or, per cubic centimeter of the device and/or the bone cement.

Accelerometers provide the benefit of being able to detect acceleration, vibration, shock, tilt, and rotation of various components. They permit the ability to measure performance of the prosthesis 10 under various conditions and over long periods of time.

During knee replacement surgery, the prosthetic joint will be moved through a full range of motion and stability testing to assess prosthetic function and mobility prior to surgical closure. The accelerometers 27 can provide the surgeon with accurate, numeric, quantitative range of motion data at that time; this data can be compared to expected values to assess efficacy of the implantation surgery and can serve as a baseline value for comparison to functional values obtained post-operatively. Any abnormalities in vibration (indicative of an inadequate anchoring of the prosthesis in the surrounding bone), tilt (indicative of improper tracking and/or alignment of the tibial-femoral joint and the patellar-femoral joint), rotation (indicative of dislocation or subluxation), and/or range of motion can be addressed at this time and allow the surgeon to make adjustments intra-operatively. Shortly after the knee has been replaced, the leg will be mobilized post-operatively, at first passively, then actively; shortly after recovering from the procedure, the patient will begin gradual weight bearing on the joint. The accelerometers 27 can measure the movement and tracking of the knee joint during movement, including during ambulation as the leg swings forward, hits the ground, plants, is lifted off the ground, and the body is propelled forward. In addition, the accelerometers can measure the impact of the foot hitting the ground and the effect of the force being transferred through the tibia to the knee joint and any vibration, shock or rotation which may occur at different locations in the prosthesis 10. As the patient continues to improve their range of motion postoperatively, the acceleration experienced at different locations in the prosthetic knee joint, can be monitored. It will be expected that as the patient heals from the surgery, activity levels will progressively increase, ambulation will improve and increase, steps will be more rapid (and fluid) and, in addition, greater stride length will be achieved with each step. The effects of exercise and various activities can be monitored by the various accelerometers 27 and can be compared to patient's subjective experiences to determine which life activities are improving (or inhibiting) post-operative recovery and rehabilitation.

Figure 8:
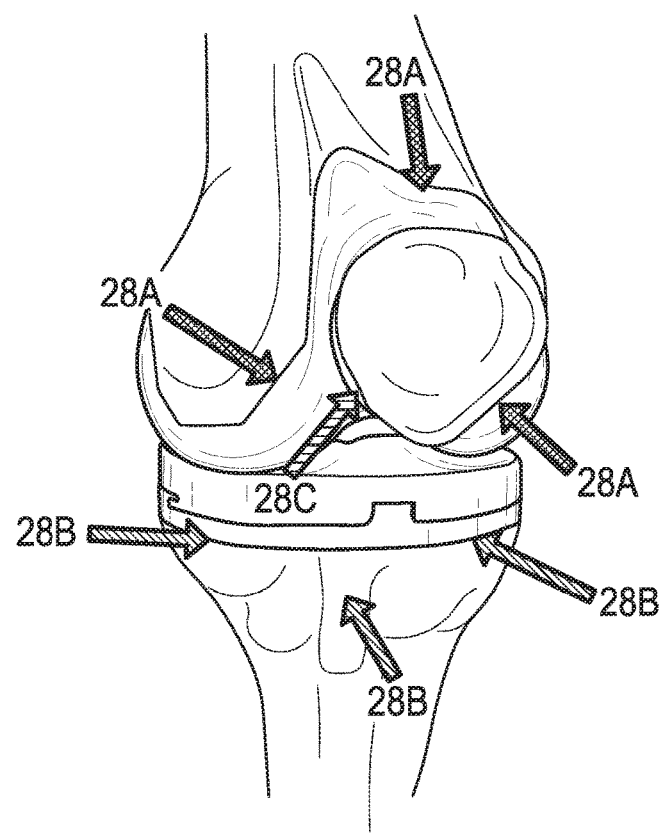
FIG. 8 illustrates a TKR with various positional sensors.

In another embodiment shown in FIG. 8, one or more position sensors 28 are provided throughout the implant, including position sensors 28A distributed on and within the femoral condyle prosthesis, position sensors 26B distributed on and within the tibial plate (and stem if present) and tibial liner, and position sensors 27C distributed on within the patellar prosthesis (patellar "button"). In some embodiments, the position sensors are on/within the prosthetic components themselves (tibial, femur and patellar segments), while in others the position sensors are contained on/within the bone cement (if present) used to secure the prosthesis to the surrounding bone, and in still other embodiments the position sensors are contained on/within both the prosthetic components and the bone cement (PMMA).

In various embodiments, position sensors may be positioned in a variety of different patterns within/on the prosthetic components based on their contact locations with respect to the surrounding bone (femur, tibia and/or patella), the surrounding bone cement (if present), the articular interface between the different prosthetic components (tibial-femoral joint and the patellar-femoral joint), and/or between sub-segments of a component (e.g. between the tibial plate and the tibial liner). For example, they may be arranged in the pattern of an X, as oval or concentric rings around, or within, the various components or in various other patterns, in order to collect accurate data experienced by the prosthetic components, the surrounding bone cement (if present), and (by extension) the surrounding bone (femur, tibia, patella) tissue.

Within various embodiments of the invention position sensors 28 are placed on the tibial component, femoral component, patellar prosthesis, and/or in the bone cement at a density of greater than one, two, three, four, five, six, seven, eight, nine, or ten sensors per square centimeter, or, per cubic centimeter of the device and/or bone cement.

Positional sensors 28 as described herein can be utilized to provide accurate positional data (intra-operatively and post-operatively), including the measurement of flexion and extension, to enhance the accuracy of a physical exam by providing 3 dimensional data of the implant, to detect full and partial dislocation (subluxation) of the tibial-femoral (knee) joint and/or the patella-femoral joint, and to determine proper tracking of the knee joint and the patella.

Figure 9:
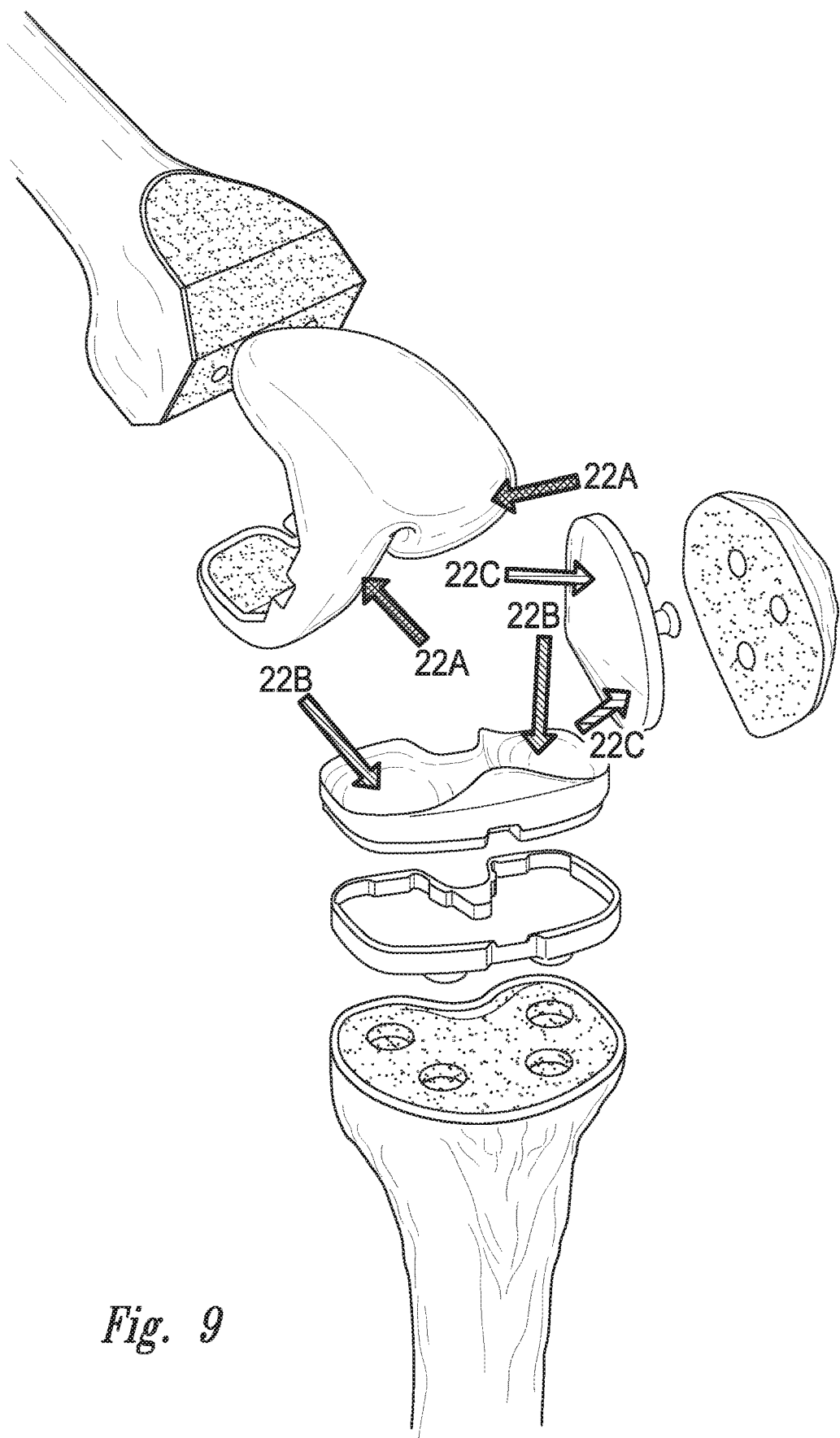
FIG. 9 illustrates a TKR with sensors placed to detect articular wear.

In another embodiment shown in FIG. 9, one or more contact or pressure sensors 22 are provided throughout the implant, including contact or pressure sensors 22A distributed on and within (at various depths) the femoral condyle articular surface, contact or pressure sensors 22B distributed on and within the tibial articular liner (at various depths), and contact or pressure sensors 27C distributed on within (at various depths) the patellar articular prosthesis (patellar "button").

These sensors can also be utilized to detect progressive erosion of the various articular surfaces. The sensors 22 may be placed at progressive depths in the tibial, femoral and patellar articular surface materials. They can also be activated when they are uncovered (or when the covering surface is worn away), to indicate the extent and depth of surface loss.

Such sensors can be utilized to estimate the effective remaining lifespan of the implant, and to compare the performance and design of different materials and implants.

B. Use of Knee Prosthesis, Medical Device or Kit to Deliver Therapeutic Agent(S)

As noted above, the present invention also provides knee prosthesis, medical devices and kits which comprise one or more sensors, and which can be utilized to release a therapeutic agent (e.g., a drug) to a desired location within the body. For example, anti-restenotic drugs (e.g., paclitaxel, sirolimus, or an analog or derivative of these), can be administered by a knee prosthesis, medical device or kit. Within preferred embodiments one or more sensors (e.g., pressure sensors, contact sensors, and/or position sensors) can be utilized to determine appropriate placement of the desired drug, as well as the quantity of drug that is released at the desired site.

Within other embodiments of the invention a wide variety of additional therapeutic agents may be delivered (e.g., to prevent or treat an infection or to treat another disease state), including for example: Anthracyclines (e.g., gentamycin, tobramycin, doxorubicin and mitoxantrone); Fluoropyrimidines (e.g., 5-FU); Folic acid antagonists (e.g., methotrexate); Podophylotoxins (e.g., etoposide); Camptothecins; Hydroxyureas, and Platinum complexes (e.g., cisplatin) (see e.g., U.S. Pat. No. 8,372,420 which is incorporated by reference in its entirety. Other therapeutic agents include beta-lactam antibiotics (e.g., the penicillins, cephalosporins, carbacephems and carbapenems); aminoglycosides (e.g., sulfonamides, quinolones and the oxazolidinones); glycopeptides (e.g., vancomycin); lincosamides (e.g, clindamycin); lipopeptides; macrolides (e.g., azithromycin); monobactams; nitrofurans; polypeptides (e.g, bacitracin); and tetracyclines.

C. Use of a Knee Prosthesis, Medical Device or Kit Having Sensors to Measure Degradation or Wearing of an Implant As noted above, within various aspects of the present invention knee prosthesis, medical devices and kits which can detect and monitor the degradation of an implant. For example, within one embodiment of the invention a method is provided for degradation of a knee replacement, medical device or kit, comprising the steps of a) providing to a subject a knee replacement, medical device or kit having sensors as described herein, and b) detecting a change in a sensor, and thus determining degradation of the knee replacement, medical device or kit. Within various embodiments the sensor(s) can detect one or more physiological and/or locational parameters. Within another embodiment, the sensor(s) can detect contact, fluid flow, pressure and/or temperature. Within yet another embodiment the sensors can detect a location within the subject.

When a knee prosthesis degrades or is damaged, sensors can detect a change so that a determination of damage and/or degradation can be made. For example, a sensor that was previously embedded within a polymer portion of a device, upon degradation may be exposed to fluid forces, and pressures where none existed before. If a sensor is eroded away, it may move within the synovial cavity (i.e., away from where it had previously been implanted). Hence, within preferred embodiments of the invention degradation can be detected over a period of time.

D. Methods for Monitoring Infection in Knee Prosthesis, Medical Devices and Kits Within other embodiments knee prosthesis, medical devices and kits are provided comprising one or more temperature and/or metabolic sensors. Such knee prosthesis, medical device or kits can be utilized to measure the temperature of the knee prosthesis, medical device or kit, and in the local tissue adjacent to the knee prosthesis, medical device or kit. Methods are also provided for monitoring changes in temperature over time, in order to determine and/or provide notice (e.g., to a patient and/or healthcare provider) that an infection may be imminent.

In certain embodiments of the present invention, metabolic and physical sensors can also be placed on or within the various components of a total or partial knee prosthesis, medical device or kit in order to monitor for rare, but potentially life-threatening complications of knee prosthesis, medical device or kits. In some patients, the knee prosthesis, medical device or kit and surrounding tissues can become infected; typically from bacteria colonizing the patient's own skin that contaminate the surgical field (often *Staphylococcus aureus* or *Staphylococcus epidermidis*). Sensors such as temperature sensors (detecting temperature increases), pH sensors (detecting pH decreases), and other metabolic sensors can be used to suggest the presence of infection on or around the implant. For example, temperature sensors may be included within one or more components of a knee prosthesis, medical device or kit in order to allow early detection of infection could allow preemptive treatment with antibiotics or surgical drainage and eliminate the need to surgically remove the knee prosthesis, medical device or kit.

Hence, within one embodiment of the invention methods are provided for determining an infection associated with a knee prosthesis, medical device or kit, comprising the steps of a) providing to a subject a knee prosthesis, medical device or kit as described herein, wherein the knee prosthesis, medical device or kit comprises at least one temperature sensor and/or metabolic sensor, and b) detecting a change in said temperature sensor and/or metabolic sensor, and thus determining the presence of an infection. Within various embodiments of the invention the step of detecting may be a series of detections over time, and a change in the sensor is utilized to assess the presence or development of an infection. Within further embodiments a change of 0.5%, 1.0%, or 1.5% elevation of temperature or a metabolic factor over time (e.g., 0.5, 1.0, 1.5, 2.0, 2.5, 3.0, 3.5, 4 hours, 12 hours, 1 day, or 2 days) can be indicative of the presence of an infection (or a developing infection).

Within various embodiments of the invention an antibiotic may be delivered in order to prevent, inhibit or treat an infection subsequent to its detection. Representative examples of suitable antibiotics are well known, and are described above under Section B (the "Therapeutic Agents").

E. Further Uses of Sensor-Containing Knee Prosthesis, Medical Devices and Kits in Healthcare Postoperative progress can be monitored (readings compared from day-to-day, week-to-week, etc.) and the information compiled and relayed to both the patient and the attending physician allowing rehabilitation to be followed sequentially and compared to expected (typical population) norms. Within certain embodiments, a wearable device interrogates the sensors on a selected or randomized basis, and captures and/or stores the collected sensor data. This data may then be downloaded to another system or device (as described in further detail below).

Integrating the data collected by the sensors described herein (e.g., contact sensors, position sensors, strain gauges and/or accelerometers) with simple, widely available, commercial analytical technologies such as pedometers and global positioning satellite (GPS) capability, allows further clinically important data to be collected such as, but not restricted to: extent of patient ambulation (time, distance, steps, speed, cadence), patient activity levels (frequency of activity, duration, intensity), exercise tolerance (work, calories, power, training effect), range of motion (discussed later) and prosthesis performance under various "real world" conditions. It is difficult to overstate the value of this information in enabling better management of the patient's recovery. An attending physician (or physiotherapist, rehabilitation specialist) only observes the patient episodically during scheduled visits; the degree of patient function at the exact moment of examination can be impacted by a multitude of disparate factors such as: the presence or absence of pain, the presence or absence of inflammation, stiffness, time of day, compliance and timing of medication use (pain medications, anti-inflammatories), recent activity and exercise levels, patient strength, mental status, language barriers, the nature of their doctor-patient relations knee, or even the patient's ability to accurately articulate their symptoms—to name just a few. Continuous monitoring and data collection can allow the patient and the physician to monitor progress objectively by supplying objective information about patient function under numerous conditions and circumstances, to evaluate how performance has been affected by various interventions (pain control, exercise, physiotherapy, anti-inflammatory medication, rest, etc.), and to compare rehabilitation progress versus previous function and future expected function. Better therapeutic decisions and better patient compliance can be expected when both the doctor and the patient have the benefit of observing the impact of various treatment modalities on patient rehabilitation, activity, function and overall performance.

The sensors used for the contact, strain, accelerometers and position detection can be an acceptable type of those generally available (see e.g., U.S. Pat. Nos. 7,450,332; 7,463,997 and 7,924,267 which describe various types of such sensors, including MEMs sensors that can act as strain gauges, accelerometers and many other sensing functions). The particular sensor described in U.S. Pat. No. 7,450,332, which detects free fall of an object and motion of an object with respect to a gravity field, would have particular benefits in being able to detect and store all the forces acting on the leg and the full motion of the leg, during passive and active motion and when it is swinging in between steps, both before, after and during impact with the ground.

Figure 4:
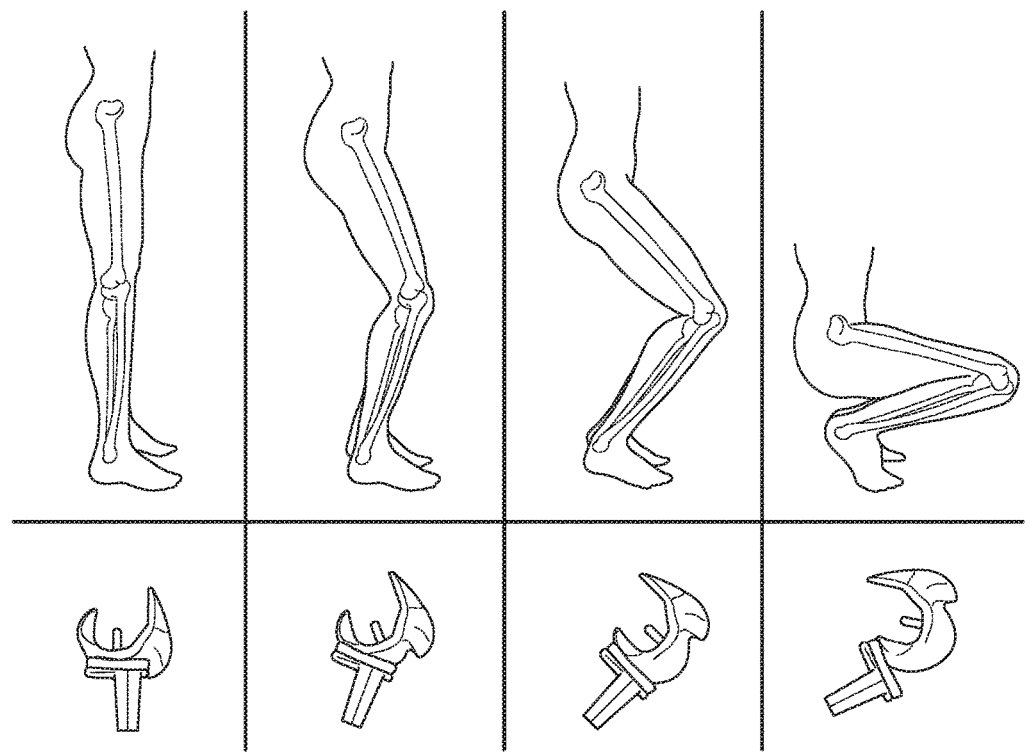
FIG. 4 illustrates a representative range of motion (ROM) for a subject with a total knee replacement.
Figure 4:
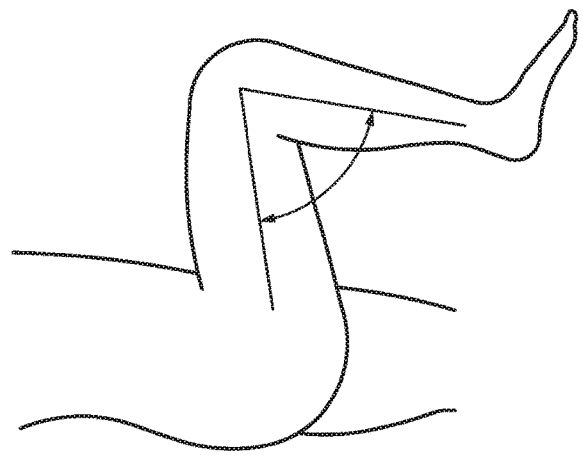

As one example of the above, FIG. 4 illustrates the uses of the sensors during a physical examination of the patient and the different types of data which may be obtained from the sensors which have been implanted according to the teachings herein. The sensors provide evaluation data on the range of motion (ROM) of the knee. Currently, ROM is usually measured clinically by the physician passively moving the knee joint through a full range of motion during physical examination and recording the results (degrees of flexion, extension, abduction, adduction, external rotation, internal rotation and rotation in flexion). Motion sensors and accelerometers can be used to accurately determine the full ROM of the prosthetic knee joint intra-operatively (in case surgical adjustment is necessary), during post-operative physical examination and during normal daily activities between visits. As shown in FIG. 11A, one primary factor in the health of the knee is the angle X that the patient is able to achieve at various times during physical therapy as they recover from the surgery. As the angle X becomes smaller and smaller, the doctor can be assured that joint function is improving. By tracking angle X over time the physical therapist can monitor the progress of the patient, assess whether scar tissue formation, subluxation, or other pathology is limiting/affecting ROM of the knee, and change/implement treatment as needed. With the sensors installed as indicated herein, the physical therapist or physician does not need to guess the angle being achieved, rather, if the leg is positioned adjacent to a read out computer, the exact angle can be known at the very moment that the joint is being clinically evaluated. On the other hand, if X does not continue to decrease, but remains large (or increases), the physical therapist or physician can be alerted to problems which the patient may be having in rehabilitation or delayed recovery from the surgery and can investigate and/or take action sooner rather than later. Similarly, the embodiment of FIG. 11B indicates measurements that can be taken when the user holds the leg at exactly a 90° angle Y as shown. With the leg held firmly at 90°, data can be collected from the various sensors throughout the leg in order to determine the strain, the contact locations, acceleration and other data. The position sensors as used herein can alert the patient that the leg is held at exactly 90° so that the collecting of the data can be accurate as data is collected at different times over several months as the patient is monitored. While flexion and extension are illustrated in the sited figures, it should be obvious to one of skill in the art that data can also be collected for medial-lateral joint stability and for anterior-posterior stability, subluxation (if present) and tracking of the knee joint and the patella. Additionally, ROM can also be monitored between patient visits by interpreting ROM generated during daily activities when the patient is at home.

As noted above, within other aspects of the invention methods are provided for imaging a knee replacement or medical device as provided herein, comprising the steps of (a) detecting the location of one or more sensors in a knee replacement or medical device; and (b) visually displaying the location of said one or more sensors, such that an image of the knee replacement or medical device is created. Within various embodiments, the step of detecting may be done over time, and the visual display may thus show positional movement over time. Within certain preferred embodiments the image which is displayed is a three-dimensional image. Within other embodiment, the imaging techniques may be utilized post-operatively in order to examine the knee replacement or medical device, and/or to compare operation and/or movement of the device over time.

Certain exemplary embodiments will now be explained in more detail. One particular benefit is the live and in-situ monitoring of the patient's recovery and the implanted prosthesis 10. The sensors as described herein are collecting data on a constant basis, during normal daily activities and even during the night if desired. Namely, the strain will be measured, collected and stored on a regular basis over long periods of time with particular measurements being taken at regular intervals. For example, the contact sensors can obtain and report data once every 10 seconds, once a minute, or once a day. Other sensors will collect data more frequently, such as several times a second. For example, it would be expected that the acceleration and position data would be collected and stored several times a second. Other types of data might only need to be collected by the minute or by the hour. Still other sensors may collect data only when signaled by the patient to do so (via an external signaling/triggering device) as part of "event recording"—i.e. when the patient experiences a particular event (e.g. pain, injury, instability, etc.)—and signals the device to obtain a reading at that time in order to allow the comparison of subjective/symptomatic data to objective/sensor data in an effort to better understand the underlying cause or triggers of the patient's symptoms. Since the tibial stem contains a large internal portion which, might be hollow or a solid bar of metal, this internal structure has more than sufficient space in order to house one or more processor circuits, CPUs, memory chips and other electrical circuits as well as antennas for sending and receiving the data. The processors can be programmed to collect data from the various sensors on any desired schedule as set by the medical professional. All activity can be continuously monitored post operation and the data collected and stored in the memory located inside the implant.

A patient will generally have regular medical checkups. When the patient goes to the doctor's office for a medical checkup, the doctor will bring a reading device closely adjacent to the prosthesis 10, in this example a knee replacement, in order to transfer the data from the internal circuit inside the implant to the database in the physician's office. The use of wireless transmission using smartcards or other techniques is very well known in the art and need not be described in detail. Examples of such wireless transmission of data are provided in the published patent applications and patents which have been described herein. The data which has been collected based on the patient's movement and use of the leg over the prior several weeks or even several months is transferred in a few moments from the memory which is positioned in the implant to the doctor's computer or wireless device. The computer therefore analyzes the data for anomalies, unexpected changes over time, positive or negative trends, and other signs which may be indicative of the health of the patient and the operability of the prosthesis. In addition, the physician can collect data that details the record of all impacts to the joint, including the magnitude and the direction of the acceleration. If the physician locates a high acceleration event, such as the patient falling, or other physical activities or exercise, the physician can be alerted to inquire of the patient of any problems they may have had during a fall or, alternatively, warn the patient against too vigorous an activity which may potentially cause damage to the knee implant. For example, if the patient has decided to go skiing or jogging, the doctor will be able to monitor the effect of such activity on the prosthesis 10, including the accelerations and strains during the event itself. The doctor can then look at the health of the prosthesis in the hours and days after the event and compare it to data prior to the event to determine if any particular event caused long term damage, such a separation of the prosthesis from the surrounding bone tissue or joint subluxation, or if the activities subjected the prosthesis to stress/strain/impact forces beyond the manufacturer's performance specifications for that particular artificial joint. Data can be collected and compared with respect to the ongoing and long term performance of the prosthesis from the strain gauges, the contact sensors, the surface wear sensors, or other sensors which may be present.

In one alternative, the patient may also have such a reading device in their home which collates the data from the prosthesis on a periodic basis, such as once per day or once per week. As described above, the patient may also be able to "trigger" a device reading (via an external signaling/triggering device) as part of "event recording." Empowering the patient to follow their own rehabilitation—and enabling them to see the positive (and negative) effects of various lifestyle choices on their health and rehabilitation—can be expected to improve compliance and improve patient outcomes. Furthermore, their experience can be shared via the web with other patients to compare their progress versus expected "norms" for function and rehabilitation and alert them to signs and symptoms that should be brought to their doctor's attention. The performance of different implants can be compared in different patients (different sexes, weights, activity levels, etc.) to help manufacturers design better prostheses and assist orthopedic surgeons in the selection of the right prosthesis for specific patient types. Payers, patients, manufacturers and physicians could all benefit from the collection of this comparative information. Lastly, data accumulated at home can be collected and transmitted via the Internet to the physician's office for analysis—potentially eliminating unnecessary visits in some cases and encouraging immediate medical follow-up in others.

F. Generation of Power

Within certain aspects of the invention, a small electrical generation unit can be positioned along an outer, or alternatively an inner, surface of the implant. In particular, every time a user takes a step, there is a release of pressure and an increase of pressure inside the internal structure of the implant. Using the appropriate piezoelectric materials or microelectric generators, a small amount of electricity can be generated with each step that is taken. The electricity can be stored in capacitors also mounted inside the implant. The electricity can then be used to power the sensors that are positioned at the various locations inside the prosthesis.

A variety of techniques have been described for scavenging power from small mechanical movements or mechanical vibration. See, for example, the article entitled "Piezoelectric Power Scavenging of Mechanical Vibration Energy," by U. K. Singh et al., as published in the Australian Mining Technology Conference, Oct. 2-4, 2007, pp. 111-118. This paper provides examples of different types of power scavengers which can produce electricity from very small motion and store the electricity for later use. The above article also describes embodiments in which pressure is applied and released from the particular structure in order to produce electricity without the need for motion, but rather as a result of the application of high pressure. As explained in the embodiments herein, force is applied to the internal structure of the implant when the patient puts his weight on the leg during a step and such force can produce more than enough electric power to operate all of the sensors which are described herein. Other mechanisms that can produce electricity from very small amounts of repetitive motion are described U.S. Patent Application Publication No. 2010/0164705, published on Jul. 1, 2010. This patent application describes techniques by which energy can be harvested in the rotation of a tire and then the harvested energy can be used to power a plurality of different sensors and then, at selected time periods, the selected sensors can output the collected data to a central collection site. Other sensors of this type are described in issued U.S. Pat. No. 7,603,894, entitled "Self-Powered Tire Monitoring System."

In one preferred embodiment, the electrical generation system is motionless and relies solely on pressure that is applied during the step and the release of that pressure when the step is completed and the leg swings free for the next step. Since there is no motion, the patent will not feel any sensation due to small changes in the position or length of the implant during the step. Rather, the length is kept constant and the electricity is generated by piezoelectric structures or by internal suspended structures which do not form part of the support structure of the implant.

After the electricity is generated by one or more generators, the electricity is transmitted to any one of the variety of sensors which is described herein. For example, it can be transmitted to the contact sensors 22, the strain gauges 26, the accelerometers 27, or the positional sensors 28. It may also be transmitted to the other sensors described herein. The transmission of the power can be carried out by any acceptable technique. For example, if the sensor is physically coupled to the implant, electric wires may run from the generator to the particular sensor. Alternatively, the electricity can be transmitted wirelessly in the same way that wireless smartcards receive power from closely adjacent power sources using the appropriate send and receive antennas. Such send and receive techniques of electric power are also described in the publication and the patent applications and issued U.S. patent previously described, all of which are incorporated herein by reference.

G. Medical Imaging and Self-Diagnosis of Assemblies Comprising Knee Replacements; Predictive Analysis and Predictive Maintenance The present invention provides knee replacements which are capable of imaging through the use of sensors over a wide variety of conditions. For example, within various aspects of the invention methods are provided for imaging a knee replacement (or portion thereof (e.g., a medical device or kit as described herein) or an assembly comprising a knee replacement, medical device or kit (as described herein) with sensors, comprising the steps of detecting the changes in sensors in, on, and or within a knee replacement, medical device or kit over time, and wherein the knee replacement, medical device or kit comprises sensors at a density of greater than 1, 2, 3, 4, 5, 6, 7, 8, 9, 10 or 10 sensors per square centimeter. Within other aspects the knee replacement medical device or kit comprises sensors at a density of greater than 1, 2, 3, 4, 5, 6, 7, 8, 9, 10 or 10 sensors per cubic centimeter. Within either of these embodiments there can be less than 50, 75, 100, or 100 sensors per square centimeter, or per cubic centimeter. Within various embodiments the at least one or more of the sensors may be placed randomly, or at one or more specific locations within the knee replacement, medical device, or kit as described herein. As noted above, a wide variety of sensors can be utilized therein, including for example, contact sensors, strain gauge sensors, pressure sensors, fluid pressure sensors, position sensors, pulse pressure sensors, blood volume sensors, blood flow sensors, blood chemistry sensors, blood metabolic sensors, mechanical stress sensors, and temperature sensors.

For example, a knee replacement, medical device, or kit comprising sensors as described herein can be utilized to image knee anatomy through sensors which can detect positional movement. The sensors used can also include accelerometers and motion sensors to detect movement of the knee replacement due to a variety of physical changes. Changes in the position of the accelerometers and/or motion sensors over time can be used as a measurement of changes in the position of the knee replacement over time. Such positional changes can be used as a surrogate marker of knee anatomy—i.e. they can form an "image" of the knee replacement to provide information on the size, shape and location of changes to the knee replacement, and/or knee replacement movement/migration. For example, loosening of the knee prosthesis can result in unwanted movement of the prosthesis relative to bone in which it is implanted during activity and weight bearing. By utilizing sensors in the present invention, it is possible to determine the location of the unwanted movement and the degree of movement present during different motions and activities. Similarly, monitoring changes in the joint space (i.e. the change in the space separating the femoral and the tibial components) over time can be used as an indicator of joint surface (femoral side and/or tibial side) erosion and wear. Finally, following the movement of the sensors throughout their range of motion can provide a dynamic "image" of the joint; allowing the clinician to monitor both improvement and decline in joint function (and surrounding tissues) over time.

H. Methods of Monitoring Assemblies Comprising Knee Replacements

Figure 10:
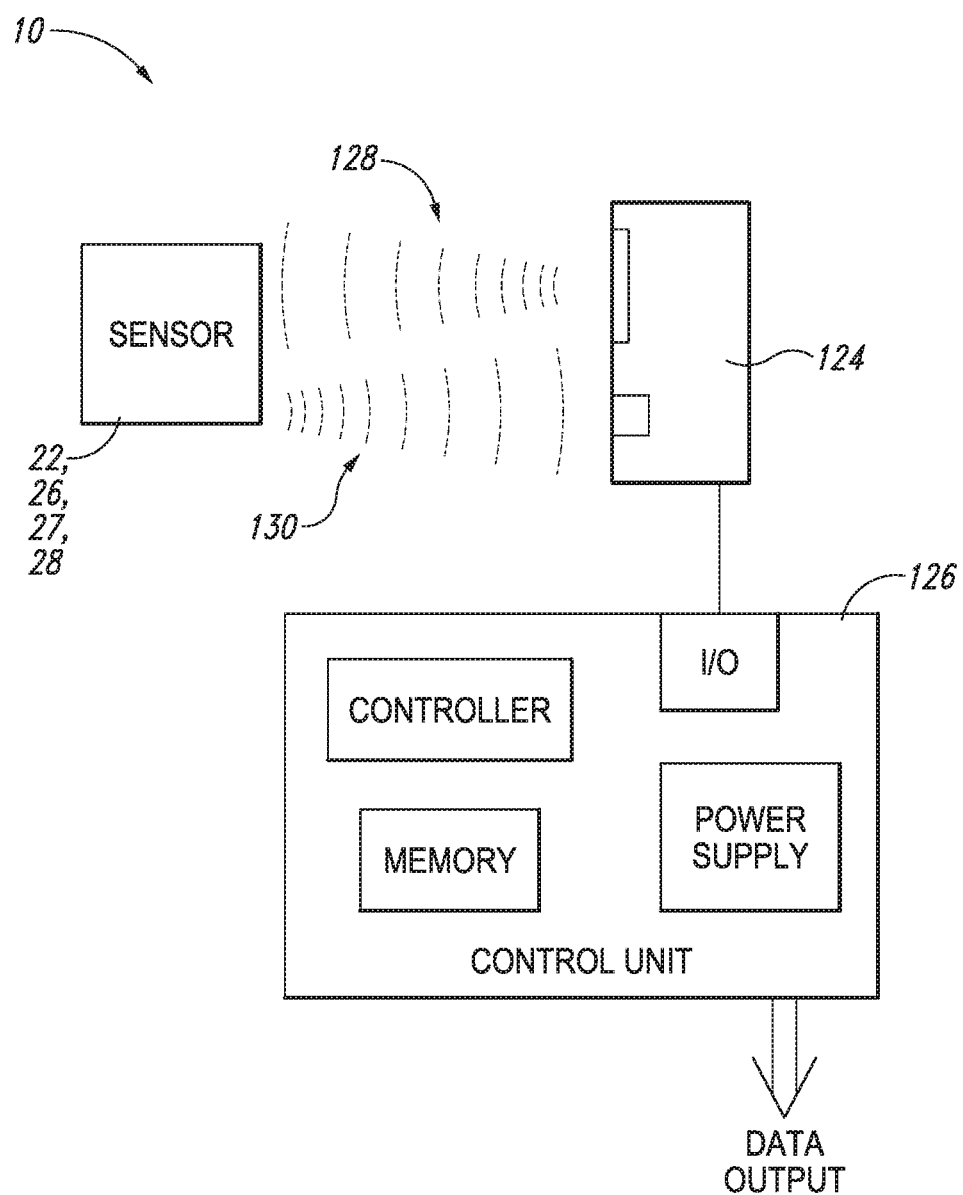
FIG. 10 illustrates an information and communication technology system embodiment arranged to process sensor data.

As noted above, the present invention also provides methods for monitoring one or more of the knee replacement assemblies provided herein. For example, FIG. 10 illustrates a monitoring system usable with the knee replacement 10 as of the type shown in any one of the Figures described above. The monitoring system includes a sensor (e.g., 22, 26, 27 and/or 28) an interrogation module 124, and a control unit 126. The sensor (e.g., 22, 26, 27 and/or 28) can be passive, wireless type which can operate on power received from a wireless source. Such sensors of this type are well known in the art and widely available. A pressure sensor of this type might be a MEMS pressure sensor, for example, Part No. LPS331AP, sold on the open market by STMicroelectronics. MEMS pressure sensors are well known to operate on very low power and suitable to remain unpowered and idle for long periods of time. They can be provided power wirelessly on an RF signal and, based on the power received wirelessly on the RF signal, perform the pressure sensing and then output the sensed data.

In one embodiment, an electrical generation system (as described above) is provided that can be utilized to power the sensors described herein. During operation, as shown in FIG. 10, an interrogation module 124 outputs a signal 128. The signal 128 is a wireless signal, usually in the RF band, that contains power for the sensor (e.g., 22, 26, 27 and/or 28) as well as an interrogation request that the sensors perform a sensing. Upon being interrogated with the signal 128, the sensor (e.g., 22, 26, 27 and/or 28) powers up and stores power in onboard capacitors sufficient to maintain operation during the sensing and data reporting. Such power receiving circuits and storing on onboard capacitors are well known in the art and therefore need not be shown in detail. The appropriate sensing is carried out by the sensor (e.g., 22, 26, 27 and/or 28) and then the data is output from the sensor back to the interrogation module 124 on a signal 130, where it is received at an input port of the integration module.

According to one embodiment, sufficient signal strength is provided in the initial signal 128 to provide power for the sensor and to carry out the sensing operation and output the signal back to the interrogation module 124. In other embodiments, two or more signals 128 are sent, each signal providing additional power to the sensor to permit it to complete the sensing operation and then provide sufficient power to transfer the data via the signal path 130 back to the interrogation module 124. For example, the signal 128 can be sent continuously, with a sensing request component at the first part of the signal and then continued providing, either as a steady signal or pulses to provide power to operate the sensor. When the sensor is ready to output the data, it sends a signal alerting the interrogation module 124 that data is coming and the signal 128 can be turned off to avoid interference. Alternatively, the integration signal 128 can be at a first frequency and the output signal 130 at a second frequency separated sufficiently that they do not interfere with each other. In a preferred embodiment, they are both the same frequency so that the same antenna on the sensor can receive the signal 128 and send signal 130.

The interrogation signal 128 may contain data to select specific sensors on the knee replacement. For example, the signal 128 may power up all sensors on the knee replacement at the same time and then send requests for data from each at different selected times so that with one interrogation signal 128 provided for a set time, such as 1-2 seconds, results in each of the sensors on the knee replacement collecting data during this time period and then, at the end of the period, reporting the data out on respective signals 130 at different times over the next 0.5 to 2 seconds so that with one interrogation signal 128, the data from all sensors 22 is collected.

The interrogation module 124 is operating under control of the control unit 126 which has a microprocessor for the controller, a memory, an 110 circuit to interface with the interrogation module and a power supply. The control unit may output data to a computer or other device for display and use by the physician to treat the subject.

Figure 11:
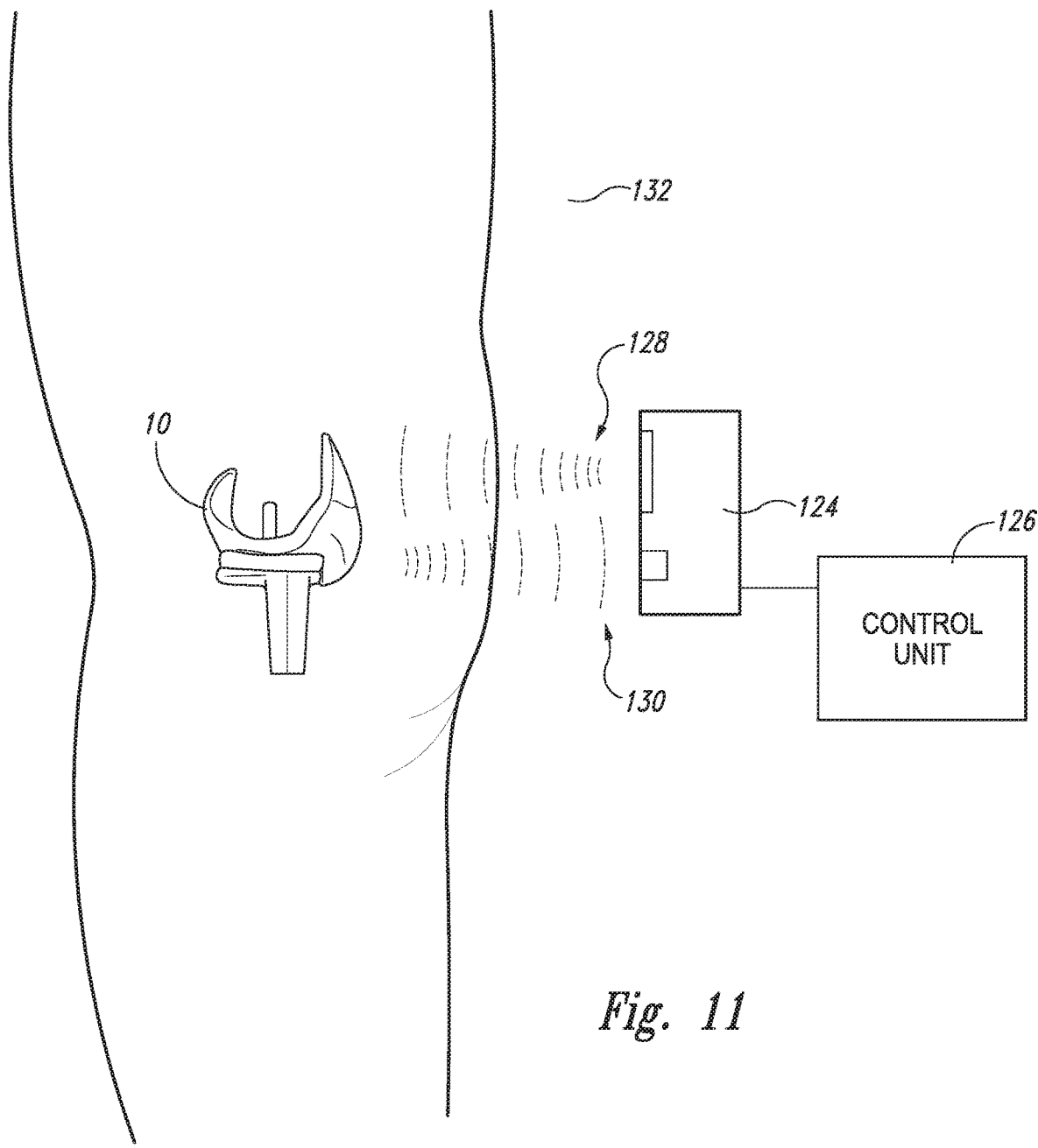
FIG. 11 is a block diagram of a sensor, interrogation module, and a control unit according to one embodiment of the invention.

FIG. 11 illustrates the operation according to a preferred embodiment within a subject. The subject has an outer skin 132. As illustrated in FIG. 13, the interrogation module 124 and control unit 126 are positioned outside the skin 132 of the subject. The interrogation signal 128 passes through the skin of the subject with a wireless RF signal, and the data is received on a wireless RF signal 130 from the sensor (e.g., 22, 26, 27 and/or 28) back to the interrogation module 124. While the wireless signal can be in any frequency range, an RF range is preferred. A frequency in the VLF to LF ranges of between 3-1300 kHz is preferred to permit the signal to be carried to sufficient depth inside the body with low power, but frequencies below 3 kHz and above 1300 kHz can also be used. The sensing does not require a transfer of large amounts of data and low power is preferred; therefore, a low frequency RF signal is acceptable. This also avoids competition from and inadvertent activation by other wireless signal generators, such as blue tooth, cell phones and the like.

Figure 12:
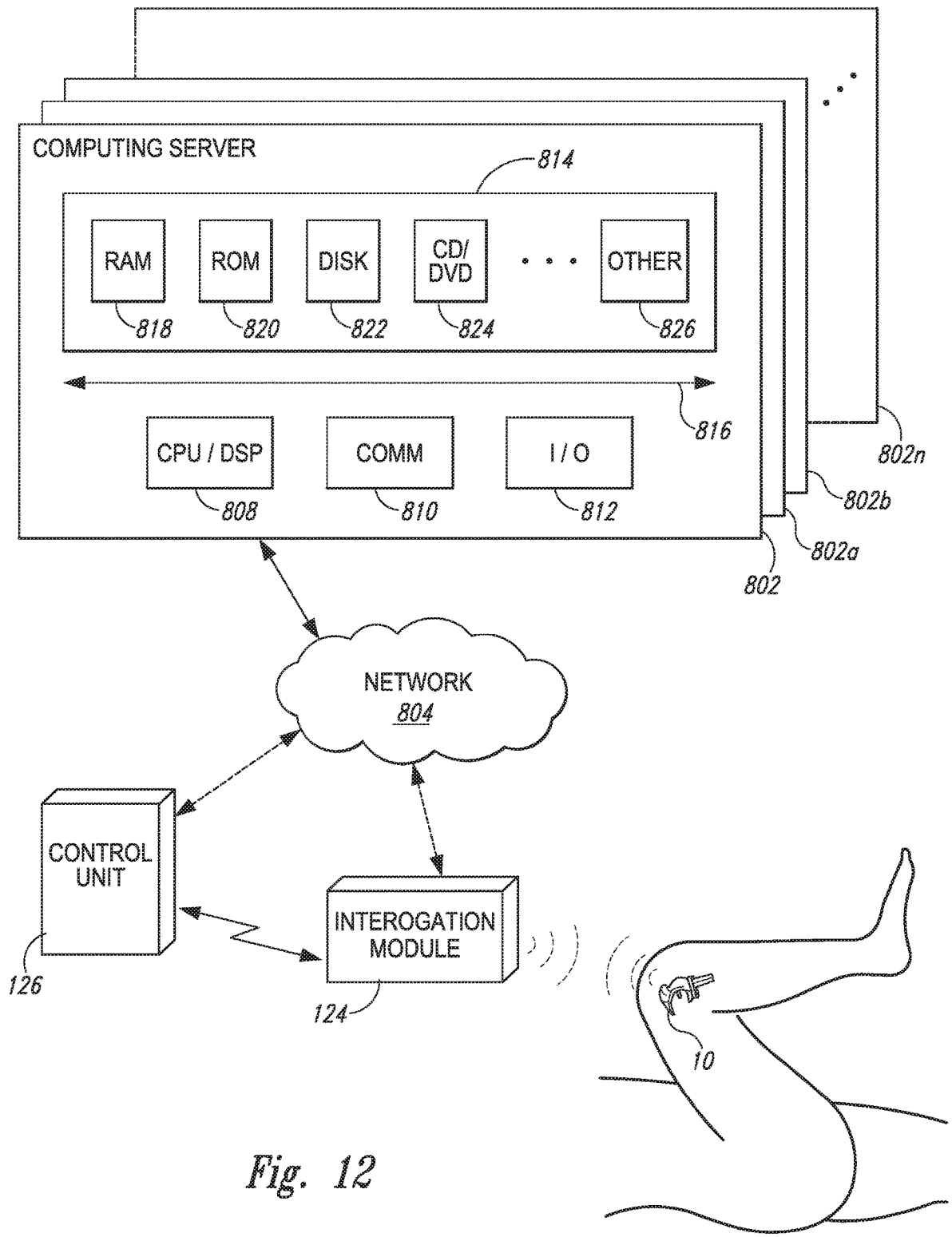
FIG. 12 is a schematic illustration of one or more sensors positioned on a knee replacement within a subject which is being probed for data and outputting data, according to one embodiment of the invention.

I. Collection, Transmission, Analysis, and Distribution of Data from Assemblies Comprising Knee Replacements FIG. 12 illustrates one embodiment of an information and communication technology (ICT) system 800 arranged to process sensor data (e.g., data from sensor (e.g., 22, 26, 27 and/or 28) of any one of Figures provided herein). In FIG. 12, the ICT system 800 is illustrated to include computing devices that communicate via a network 804, however in other embodiments, the computing devices can communicate directly with each other or through other intervening devices, and in some cases, the computing devices do not communicate at all. The computing devices of FIG. 12 include computing servers 802, control units 126, interrogation units 124, and other devices that are not shown for simplicity.

In FIG. 12, one or more sensors (e.g., 22, 26, 27 and/or 28) communicate with an interrogation module 124. The interrogation module 124 of FIG. 12 is directed by a control unit 126, but in other cases, interrogation modules 124 operates autonomously and passes information to and from sensors 22. One or both of the interrogation module 124 and control unit 126 can communicate with the computing server 802.

Within certain embodiments, the interrogation module and/or the control unit may be a wearable device on the subject. The wearable device (e.g., a watch-like device, glasses, a wrist-band, or other device that may be carried or worn by the subject) can interrogate the sensors over a set (or random) period of time, collect the data, and forward the data on to one or more networks (804). Furthermore, the wearable device may collect data of its own accord which can also be transmitted to the network. Representative examples of data that may be collected include location (e.g., a GPS), body or skin temperature, and other physiologic data (e.g., pulse). Within yet other embodiments, the wearable device may notify the subject directly of any of a number of prescribed conditions, including but not limited to possible or actual failure of the device.

The information that is communicated between an interrogation module 124 and a sensor (e.g., 22, 26, 27 and/or 28) may be useful for many purposes as described herein. In some cases, for example, sensor data information is collected and analyzed expressly for the health of an individual subject. In other cases, sensor data is collected and transmitted to another computing device to be aggregated with other data (for example, the sensor data from 22 may be collected and aggregated with other data collected from a wearable device (e.g., a device that may, in certain embodiments, include GPS data and the like).

FIG. 12 illustrates aspects of a computing server 802 as a cooperative bank of servers further including computing servers 802a, 802b, and one or more other servers 802n. It is understood that computing server 802 may include any number of computing servers that operate individually or collectively to the benefit of users of the computing servers.

In some embodiments, the computing servers 802 are arranged as cloud computing devices created in one or more geographic locations, such as the United States and Canada. The cloud computing devices may be created as MICROSOFT AZURE cloud computing devices or as some other virtually accessible remote computing service.

An interrogation module 124 and a control unit 126 are optionally illustrated as communicating with a computing server 802. Via the interrogation module 124 or control unit 126, sensor data is transferred to (and in addition or alternatively from) a computing server 802 through network 804.

The network 804 includes some or all of cellular communication networks, conventional cable networks, satellite networks, fiber-optic networks, and the like configured as one or more local area networks, wide area networks, personal area networks, and any other type of computing network. In a preferred embodiment, the network 804 includes any communication hardware and software that cooperatively works to permit users of computing devices to view and interact with other computing devices.

Computing server 802 includes a central processing unit (CPU) digital signal processing unit (DSP) 808, communication modules 810, Input/Output (I/O) modules 812, and storage module 814. The components of computing server 802 are cooperatively coupled by one or more buses 816 that facilitate transmission and control of information in and through computing server 802. Communication modules 810 are configurable to pass information between the computer server 802 and other computing devices (e.g., computing servers 802a, 802b, 802n, control unit 126, interrogation unit 124, and the like). I/O modules 812 are configurable to accept input from devices such as keyboards, computer mice, trackballs, and the like. I/O modules 812 are configurable to provide output to devices such as displays, recorders, LEDs, audio devices, and the like.

Storage module 814 may include one or more types of storage media. For example, storage module 814 of FIG. 12 includes random access memory (RAM) 818, read only memory (ROM) 810, disk based memory 822, optical based memory 8124, and other types of memory storage media 8126. In some embodiments one or more memory devices of the storage module 814 has configured thereon one or more database structures. The database structures may be used to store data collected from sensors 22.

In some embodiments, the storage module 814 may further include one or more portions of memory organized a non-transitory computer-readable media (CRM). The CRM is configured to store computing instructions executable by a CPU 808. The computing instructions may be stored as one or more files, and each file may include one or more computer programs. A computer program can be standalone program or part of a larger computer program. Alternatively or in addition, each file may include data or other computational support material for an application that directs the collection, analysis, processing, and/or distribution of data from sensors (e.g., knee replacement sensors). The sensor data application typically executes a set of instructions stored on computer-readable media.

It will be appreciated that the computing servers shown in the figures and described herein are merely illustrative and are not intended to limit the scope of the present invention. Computing server 802 may be connected to other devices that are not illustrated, including through one or more networks such as the Internet or via the Web that are incorporated into network 804. More generally, a computing system or device (e.g., a "client" or "server") or any part thereof may comprise any combination of hardware that can interact and perform the described types of functionality, optionally when programmed or otherwise configured with software, including without limitation desktop or other computers, database servers, network storage devices and other network devices, PDAs, cell phones, wireless phones, glasses, wrist-bands, pagers, electronic organizers, Internet appliances, television-based systems (e.g., using set-top boxes and/or personal/digital video recorders), and various other products that include appropriate inter-communication capabilities. In addition, the functionality provided by the illustrated system modules may in some embodiments be combined in fewer modules or distributed in additional modules. Similarly, in some embodiments the functionality of some of the illustrated modules may not be provided and/or other additional functionality may be available.

In addition, while various items are illustrated as being stored in memory or on storage while being used, these items or portions of them can be transferred between memory and other storage devices for purposes of memory management and/or data integrity. In at least some embodiments, the illustrated modules and/or systems are software modules/systems that include software instructions which, when executed by the CPU/DSP 808 or other processor, will program the processor to automatically perform the described operations for a module/system. Alternatively, in other embodiments, some or all of the software modules and/or systems may execute in memory on another device and communicate with the illustrated computing system/device via inter-computer communication.

Furthermore, in some embodiments, some or all of the modules and/or systems may be implemented or provided in other manners, such as at least partially in firmware and/or hardware means, including, but not limited to, one or more application-specific integrated circuits (ASICs), standard integrated circuits, controllers (e.g., by executing appropriate instructions, and including microcontrollers and/or embedded controllers), field-programmable gate arrays (FPGAs), complex programmable logic devices (CPLDs), and the like. Some or all of the systems, modules, or data structures may also be stored (e.g., as software instructions or structured data) on a transitory or non-transitory computer-readable storage medium 814, such as a hard disk 822 or flash drive or other non-volatile storage device 8126, volatile 818 or non-volatile memory 810, a network storage device, or a portable media article (e.g., a DVD disk, a CD disk, an optical disk, a flash memory device, etc.) to be read by an appropriate input or output system or via an appropriate connection. The systems, modules, and data structures may also in some embodiments be transmitted as generated data signals (e.g., as part of a carrier wave or other analog or digital propagated signal) on a variety of computer readable transmission mediums, including wireless-based and wired/cable-based mediums. The data signals can take a variety of forms such as part of a single or multiplexed analog signal, as multiple discrete digital packets or frames, as a discrete or streaming set of digital bits, or in some other form. Such computer program products may also take other forms in other embodiments. Accordingly, the present invention may be practiced with other computer system configurations.

In FIG. 12, sensor data from, e.g., sensor (e.g., 22, 26, 27 and/or 28) is provided to computing server 802. Generally speaking, the sensor data, represents data retrieved from a known subject and from a known sensor. The sensor data may possess include or be further associated with additional information such as the USI, UDI, a time stamp, a location (e.g., GPS) stamp, a date stamp, and other information. The differences between various sensors is that some may include more or fewer data bits that associate the data with a particular source, collection device, transmission characteristic, or the like.

In some embodiments, the sensor data may comprise sensitive information such as private health information associated with a specific subject. Sensitive information, for example sensor data from sensor (e.g., 22, 26, 27 and/or 28), may include any information that an associated party desires to keep from wide or easy dissemination. Sensitive information can stand alone or be combined with other non-sensitive information. For example, a subject's medical information is typically sensitive information. In some cases, the storage and transmission of a subject's medical information is protected by a government directive (e.g., law, regulation, etc.) such as the U.S. Health Insurance Portability and Accountability Act (KNEEPA).

As discussed herein, a reference to "sensitive" information includes information that is entirely sensitive and information that is some combination of sensitive and non-sensitive information. The sensitive information may be represented in a data file or in some other format. As used herein, a data file that includes a subject's medical information may be referred to as "sensitive information." Other information, such as employment information, financial information, identity information, and many other types of information may also be considered sensitive information.

A computing system can represent sensitive information with an encoding algorithm (e.g., ASCII), a well-recognized file format (e.g., PDF), or by some other format. In a computing system, sensitive information can be protected from wide or easy dissemination with an encryption algorithm.

Generally speaking, sensitive information can be stored by a computing system as a discrete set of data bits. The set of data bits may be called "plaintext." Furthermore, a computing system can use an encryption process to transform plaintext using an encryption algorithm (i.e., a cipher) into a set of data bits having a highly unreadable state (i.e., cipher text). A computing system having knowledge of the encryption key used to create the cipher text can restore the information to a plaintext readable state. Accordingly, in some cases, sensitive data (e.g., sensor data 806a, 806b) is optionally encrypted before being communicated to a computing device.

In one embodiment, the operation of the information and communication technology (ICT) system 800 of FIG. 12 includes one or more sensor data computer programs stored on a computer-readable medium. The computer program may optionally direct and/or receive data from one or more knee replacement sensors implanted in one or more subjects. A sensor data computer program may be executed in a computing server 802. Alternatively, or in addition, a sensor data computer program may be executed in a control unit 126, an interrogation unit 124.

In one embodiment, a computer program to direct the collection and use of knee replacement sensor data is stored on a non-transitory computer-readable medium in storage module 814. The computer program is configured to identify a subject who has a wireless knee replacement inserted in his or her body. The wireless knee replacement may include one or more wireless sensor In some cases, the computer program identifies one subject, and in other cases, two or more subjects are identified. The subjects may each have one or more wireless knee replacements, and each wireless knee replacement may have one or more wireless sensors of the type described herein.

The computer program is arranged to direct the collection of sensor data from the wireless knee replacement devices. The sensor data is generally collected with a wireless interrogation unit 124. In some cases, the program communicates with the wireless interrogation unit 124. In other cases, the program communicates with a control unit 126, which in turn directs a wireless interrogation unit 124. In still other cases, some other mechanism is used direct the collection of the sensor data.

Once the sensor data is collected, the data may be further processed. For example, in some cases, the sensor data includes sensitive subject data, which can be removed or disassociated with the data. The sensor data can be individually stored (e.g., by unique sensor identification number, device number, etc.) or aggregated together with other sensor data by sensor type, time stamp, location stamp, date stamp, subject type, other subject characteristics, or by some other means.

The following pseudo-code description is used to generally illustrate one exemplary algorithm executed by a computing server 802 and generally described herein with respect to FIG. 12:

Start
   Open a secure socket layer (SSL)
   Identify a subject
   Communicate with a predetermined control unit
   Request sensor data from the subject via the control unit
   Receive sensor data
   If the sensor data is encrypted
   THEN decrypt the sensor data
   Store encrypted data in the selected storage locations
   Aggregate the sensor data with other sensor data
   Store encrypted data in the selected storage locations
   Maintain a record of the storage transaction
   Perform post storage actions
End Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

In conclusion, prosthetic knee replacements utilizing a variety of sensors can be utilized to serve a variety of critical clinical functions, such as safe, accurate and less traumatic placement and deployment of the knee replacement, procedural and post-operative "real time" imaging of knee replacement and the surrounding anatomy, the development of knee replacement complications, and the patient's overall health status. Currently, post-operative (both in hospital and out-patient) evaluation of knee replacement patients is through patient history, physical examination and medical monitoring that is supplemented with diagnostic imaging studies as required. However, most of the patient's recuperative period occurs between hospital and office visits and the majority of data on daily function goes uncaptured; furthermore, monitoring patient progress through the use of some diagnostic imaging technology can be expensive, invasive and carry its own health risks (the use of nuclear isotopes or certain dyes). It can, therefore, be very difficult to accurately measure and follow the development or worsening of symptoms and evaluate "real life" knee replacement performance, particularly as they relate to patient activity levels, exercise tolerance, and the effectiveness of rehabilitation efforts and medications.

At present, neither the physician nor the patient has access to the type of "real time," continuous, objective, knee replacement performance measurements that they might otherwise like to have. Being able to monitor in situ knee replacement function, integrity, anatomy and physiology can provide the physician with valuable objective information during office visits; furthermore, the patient can take additional readings at home at various times (e.g. when experiencing pain, during exercise, after taking medications, etc.) to provide important complementary clinical information to the doctor (which can be sent to the healthcare provider electronically even from remote locations). From the perspective of the patient, being able to monitor many of these same parameters at home allows them to take a more proactive role in their care and recovery and provide him or her with either an early warning indicator to seek medical assistance or with reassurance.

In one alternative, the patient may have a reading device in their home which collates the data from the knee replacement on a periodic basis, such as once per day or once per week. In addition to empowering the patient to follow their own rehabilitation—and enabling them to see the positive (and negative) effects of various lifestyle choices on their health and rehabilitation—such information access can be expected to improve compliance and improve patient outcomes. For example, within certain embodiments the devices and systems provided herein can instruct or otherwise notify the patient, or a permitted third-party as to deviations (e.g., greater than 10%, 20%, 25%, 50%, 70%, and or 100%) from normal, and/or, set parameters. Furthermore, their recovery experience can be shared via the web with other patients to compare their progress versus expected "norms" for function and rehabilitation and alert them to signs and symptoms that should be brought to their doctor's attention. From a public health perspective, the performance of different knee replacements can be compared in different patients (different sexes, disease severity, activity levels, concurrent diseases such as hypertension and diabetes, smoking status, obesity, etc.) to help manufacturers design better knee replacements and assist physicians in the selection of the right knee replacement for a specific patient types. Payers, patients, manufacturers and physicians could all benefit from the collection of this comparative information. Poor and dangerous products could be identified and removed from the market and objective long-term effectiveness data collected and analyzed. Lastly, data accumulated at home can be collected and transmitted via the Internet to the physician's office for analysis—potentially eliminating unnecessary visits in some cases and encouraging immediate medical follow-up in others.

The following are some specific numbered embodiments of the systems and processes disclosed herein. These embodiments are exemplary only. It will be understood that the invention is not limited to the embodiments set forth herein for illustration, but embraces all such forms thereof as come within the scope of the above disclosure.

1) A knee replacement prosthesis comprising:
at least one of a tibial component, a patellar prosthesis, and a femoral component; and
a plurality of sensors coupled to at least one of the tibial component, patellar prosthesis, and femoral component.

2) The knee replacement prosthesis of embodiment 1 wherein the plurality of sensors includes a sensor on the tibial component.

3) The knee replacement prosthesis of embodiment 1 wherein the plurality of sensors includes a sensor on the patellar prosthesis.

4) The knee replacement prosthesis of embodiment 1 wherein the plurality of sensors includes a sensor on the femoral component.

5) The knee replacement prosthesis according to any one of embodiments 1 to 4 wherein said sensor is selected from the group consisting of accelerometers, pressure sensors, contact sensors, position sensors, chemical microsensors, tissue metabolic sensors, mechanical stress sensors and temperature sensors.

6) The knee replacement prosthesis according to embodiment 5 wherein said accelerometer detects acceleration, tilt, vibration, shock and or rotation.

7) The knee replacement prosthesis of embodiment 1 wherein the plurality of sensors includes contact sensors positioned on the femoral component.

8) The knee replacement prosthesis of embodiment 1 wherein the plurality of sensors includes a plurality of contact sensors positioned on the patellar component.

9) The knee replacement prosthesis of embodiment 1 wherein the plurality of sensors includes a plurality of contact sensors positioned on the tibial component.

10) A medical device, comprising a femoral component of a knee replacement prosthesis and a plurality of sensors coupled to said femoral component.

11) A medical device, comprising a patellar prosthesis of a knee replacement prosthesis and a plurality of sensors coupled to said patellar prosthesis.

12) A medical device, comprising a tibial component of a knee replacement and a plurality of sensors coupled to said tibial component.

13) The medical device according to any one of embodiments 10 to 12, wherein said sensors appear within and/or on the surface of said medical device.

14) The medical device according to any one of embodiments 10 to 13 wherein said sensor is selected from the group consisting of accelerometers, pressure sensors, contact sensors, position sensors, chemical microsensors, tissue metabolic sensors, mechanical stress sensors and temperature sensors.

15) The medical device according to embodiment 14 wherein said accelerometer detects acceleration, tilt, vibration, shock and or rotation.

16) The knee replacement prosthesis according to any one of embodiments 1 to 9 or medical device according to any one of embodiments 10 to 15 further comprising:
an electronic processor positioned upon and/or inside at least one of the tibial component, patellar prosthesis and/or the femoral component that is electrically coupled to sensors.

17) The knee replacement prosthesis or medical device of embodiment 16 wherein the electric coupling is a wireless coupling.

18) The knee replacement prosthesis or medical device of embodiment 17 further including:
a memory coupled to the electronic processor and positioned upon and/or inside the at least one of tibial component, patellar prosthesis and femoral component.

19) The knee replacement prosthesis or medical device according to any one of embodiments 1 to 18 wherein said sensor is a plurality of sensors which are positioned on or within said knee replacement at a density of greater than 1, 2, 3, 4, 5, 6, 7, 8, 9, 10 or 20 sensors per square centimeter.

20) The knee replacement or medical device according to any one of embodiments 1 to 19 wherein said sensor is a plurality of sensors which are positioned on or within said knee replacement at a density of greater than 1, 2, 3, 4, 5, 6, 7, 8, 9, 10 or 20 sensors per cubic centimeter.

21) A method comprising:
obtaining contact data from contact sensors positioned at a plurality of locations between on and/or within a knee replacement prosthesis or medical devices according to any one of embodiments 1 to 20 of a patient;
storing the data in a memory device located on or within the knee replacement prosthesis or medical device; and
transferring the data from the memory to a location outside the knee replacement prosthesis or medical device.

22) The method according to embodiment 22 further including:
obtaining strain data from strain sensors positioned at a plurality of locations on the knee replacement prosthesis or medical device of a patient;
storing the strain data in a memory located in said knee replacement prosthesis or medical device; and
transferring the strain data from the memory to a memory in located outside the knee replacement prosthesis or medical device.

23) The method according to embodiment 22 further including:
obtaining contact data from contact sensors positioned in a knee replacement prosthesis or medical device according to any one of embodiments 1 to 19 of a patient;
storing the contact data in a memory located in the knee replacement prosthesis or medical device; and
transferring the data from the memory to a memory in a location outside of the knee replacement prosthesis or medical device.

24) A method comprising:
obtaining acceleration data from accelerometers positioned at a plurality of locations on a knee replacement prosthesis or medical device according to any one of embodiments 1 to 19 located in-situ in the knee of a patient;
storing the acceleration data in a memory located in the knee replacement prosthesis or medical device; and transferring the acceleration data from the said memory in the knee replacement prosthesis or medical device to a memory in a location outside the knee replacement prosthesis or medical device.

25) A kit comprising the knee replacement prosthesis or medical device according to any one of embodiments 1 to 19, further comprising bone cement and/or bone screws comprising one or more sensors.

26) The kit according to embodiment 25 wherein said one or more sensors are selected from the group consisting of accelerometers, pressure sensors, contact sensors, position sensors, chemical microsensors, tissue metabolic sensors, mechanical stress sensors and temperature sensors.

27) The kit according to embodiments 25 or 26 wherein said sensors appear on said prosthesis or medical device at a density of greater than 1, 2, 3, 4, 5, 6, 7, 8, 9, 10 or 20 sensors per square centimeter.

28) The knee replacement, medical device, or kit according to any one of embodiments 1-20 or 25-27 wherein the one or more of the sensors are placed randomly within the knee replacement, medical device or kit. Within other embodiments said sensors can be placed at specific locations within the knee replacement, medical device or kit.

29) A method for detecting and/or recording an event in a subject with a knee replacement or medical device as provided in any one of embodiments 1 to 28, comprising the step of interrogating at a desired point in time the activity of one or more sensors within the knee replacement or medical device, and recording said activity.

30) The method according to embodiment 29 wherein the step of interrogating is performed by a subject which has an implanted knee replacement or medical device.

31) The method according to embodiment 30 wherein said recording is performed on a wearable device.

32) The method according to any one of embodiments 29 to 31, wherein said recording is provided to a health care provider.

33) A method for imaging a knee replacement, medical device or kit according to any one of embodiments 1 to 20 or 25 to 27, comprising the steps of
 (a) detecting the location of one or more sensors in a knee replacement, medical device, or kit according to any one of embodiments 1 to 20 or 25 to 27; and
 (b) visually displaying the location of said one or more sensors, such that an image of the knee replacement or medical device is created.

34) The method according to embodiment 33 wherein the step of detecting occurs over time.

35) The method according to embodiment 34, wherein said visual display shows changes in the positions of said sensors over time.

36) The method according to any one of embodiments 33 to 35 wherein said visual display is a three-dimensional image of said knee replacement or medical device.

37) A method for inserting a knee replacement, medical device or kit according to any one of embodiments 1 to 20 or 25 to 27, comprising the steps of
 (a) inserting a medical device according to any one of embodiments 1 to 20 or 25 to 27 into a subject; and
 (b) imaging the placement of said medical device according to the method of any one of embodiments 33 to 36.

38) A method for examining a knee replacement, medical device or kit according to any one of embodiments 1 to 20 or 25 to 27 which has been previously inserted into a patient, comprising the step of imaging the knee replacement or medical device according to the method of any one of embodiments 33 to 36.

39) A method of monitoring a knee replacement, medical device, or kit within a subject, comprising:
 transmitting a wireless electrical signal from a location outside the body to a location inside the subject's body;
 receiving the signal at a sensor positioned on a knee replacement, medical device, or kit according to any one of embodiments 1 to 20 or 25 to 27 located inside the body;
 powering the sensor using the received signal;
 sensing data at the sensor; and
 outputting the sensed data from the sensor to a receiving unit located outside of the body.

40) The method according to embodiment 39 wherein said receiving unit is a watch, wrist band, cell phone or glasses.

41) The method according to embodiments 39 or 40 wherein said receiving unit is located within a subject's residence or office.

42) The method according to embodiments any one of embodiments 39 to 41 wherein said sensed data is provided to a health care provider.

43) The method according to any one of embodiments 39 to 42 wherein said sensed data is posted to one or more websites.

44) A non-transitory computer-readable storage medium whose stored contents configure a computing system to perform a method, the method comprising:
 identifying a subject, the identified subject having at least one wireless knee replacement, medical device, or kit according to any one of embodiments 1 to 20 or 25 to 27, each wireless knee replacement, medical device, or kit having one or more wireless sensors;
 directing a wireless interrogation unit to collect sensor data from at least one of the respective one or more wireless sensors; and
 receiving the collected sensor data.

45) The non-transitory computer-readable storage medium of embodiment 44 whose stored contents configure a computing system to perform a method, the method further comprising:
 identifying a plurality of subjects, each identified subject having at least one wireless knee replacement, medical device, or kit, each wireless knee replacement, medical device, or kit having one or more wireless sensors;
 directing a wireless interrogation unit associated with each identified subject to collect sensor data from at least one of the respective one or more wireless sensors;
 receiving the collected sensor data; and
 aggregating the collected sensor data.

46) The non-transitory computer-readable storage medium of embodiment 44 whose stored contents configure a computing system to perform a method, the method further comprising:
 removing sensitive subject data from the collected sensor data; and
 parsing the aggregated data according to a type of sensor.

47) The non-transitory computer-readable storage medium of embodiment 44 whose stored contents configure a computing system to perform a method, wherein directing the wireless interrogation unit includes directing a control unit associated with the wireless interrogation unit.

48) The non-transitory computer readable storage medium according to any one of embodiments 44 to 47, wherein said knee replacement, medical device, or kit is an assembly according to any one of embodiments 1 to 20 or 25 to 27.

49) The storage medium according to any one of embodiments 44 to 48 wherein said collected sensor data is received on a watch, wrist band, cell phone or glasses.

50) The storage medium according to any one of embodiments 44 to 49 wherein said collected sensor data is received within a subject's residence or office.

51) The storage medium according to any one of embodiments 44 to 50 wherein said collected sensed data is provided to a health care provider.

52) The storage medium according to any one of embodiments 44 to 51 wherein said sensed data is posted to one or more websites.

53) The method according to any one of embodiments 39 to 43, or storage medium according to any one of embodiments 44 to 52, wherein said data is analyzed. Within certain embodiments the data can be analyzed to assess range of motion of a subject. Within other embodiments, the data can be analyzed to assess or detect bone erosion, inflammation, surface wear, and/or deterioration and/or possible breakage or breakage of the knee prosthesis, medical device or kit (or any portion thereof).

54) The method or storage medium according to embodiment 53 wherein said data is plotted to enable visualization of change over time.

55) The method or storage medium according to embodiments 53 or 54 wherein said data is plotted to provide a three-dimensional image.

56) A method for determining degradation of a knee replacement, medical device or kit, comprising the steps of a) providing to a subject a knee replacement, medical device or kit according to any one of embodiments 1 to 20 or 25 to 27, and b) detecting a change in a sensor, and thus determining degradation of the knee replacement, medical device or kit.

57) The method according to embodiment 56 wherein said sensor is capable of detecting one or more physiological and/or locational parameters.

58) The method according to embodiment 56 or 57 wherein said sensor detects contact, fluid flow, pressure and/or temperature.

59) The method according to any one of embodiments 56 to 58 wherein said sensor detects a location within the subject.

60) The method according to any one of embodiments 56 to 59 wherein said sensor moves within the body upon degradation of the knee replacement.

61) The method according to any one of embodiments 56 to 60 wherein the step of detecting is a series of detections over time.

62) A method for determining an infection associated with a knee replacement, medical device or kit comprising the steps of a) providing to a subject a knee replacement, medical device or kit according to any one of embodiments 1 to 20 or 25 to 27, wherein said knee replacement, medical device or kit comprises at least one temperature sensor and/or metabolic sensor, and b) detecting a change in said temperature sensor and/or metabolic sensor, and thus determining the presence of an infection.

63) The method according to embodiment 62 wherein the step of detecting is a series of detections over time.

64) The method according to embodiments 62 or 63 wherein said change is greater than a 1% change over the period of one hour.

65) The method according to embodiments 62 to 64 wherein said change is a continually increasing temperature and/or metabolic activity over the course of 4 hours.

The various embodiments described above can be combined to provide further embodiments. All of the U.S. patents, U.S. patent application publications, U.S. patent applications, foreign patents, foreign patent applications and non-patent publications referred to in this specification are incorporated herein by reference, in their entirety. Aspects of the embodiments can be modified, if necessary to employ concepts of the various patents, applications and publications to provide yet further embodiments.

In general, in the following embodiments, the terms used should not be construed to limit the embodiments to the specific embodiments disclosed in the specification and the embodiments, but should be construed to include all possible embodiments along with the full scope of equivalents to which such embodiments are entitled. Accordingly, the embodiments are not limited by the disclosure.

What is claimed is:

1. A tibial component comprising:
an accelerometer and a motion sensor positioned within the tibial component, where the accelerometer is an acceleration sensor that measures acceleration and the motion sensor is a rotation sensor that measures rotation;
an electronic processor positioned within the tibial component, where the electronic processor is electrically coupled to the acceleration sensor and to the rotation sensor;
a memory chip positioned within the tibial component, where the memory chip is coupled to the electronic processor and is configured to store the measures of acceleration from the acceleration sensor and the measures of rotation from the rotation sensor;
an antenna configured to transmit the measures of acceleration and rotation from the memory chip to a location outside of the tibial component; and
a plurality of sensors, each at a different depth relative to an articular surface of the tibial component, wherein the tibial component is formed of a material and the plurality of sensors are at progressive depths within the material and are covered by a surface of the material and each sensor of the plurality of sensors is configured to activate in response to the sensor no longer being covered by the surface of the material;
wherein the tibial component comprises a first segment adjacent to a second segment, and further comprises a first contact sensor associated with the first segment and a second contact sensor associated with the second segment, wherein the first contact sensor and the second contact sensor are paired, and wherein the first segment comprises a tibial plate and the second segment comprises a tibial lining and the pairing is indicative of an accurate fitting of the tibial lining with the tibial plate.

2. The tibial component of claim 1 wherein the acceleration sensor and the motion sensor are each a microelectromechanical systems ("MEMS") or nanoelectromechanical systems ("NEMS") sensor.

3. The tibial component of claim 1 wherein the accelerometer and motion sensor are positioned within a tibial stem of the tibial component.

4. The tibial component of claim 1 further comprising a strain gauge positioned on a surface of the tibial component.

5. The tibial component of claim 4 wherein the surface is an articular surface of the tibial component, and the strain gauge provides measures indicative of mechanical strain across the articular surface of the tibial component.

6. The tibial component of claim 1, further comprising:
an electrical generation unit electrically coupled to the accelerometer and the motion sensor, where the electrical generation unit is configured to harvest energy and provide power to the accelerometer and the motion sensor.

7. The tibial component of claim 6, wherein the electrical generation unit is configured to harvest energy from motion of the tibial component.

8. The tibial component of claim 6, wherein the electrical generation unit is configured to harvest energy from pressure applied to the tibial component.

9. A method of measuring an extent of surface loss of a tibial component according to claim 1, the method comprising:
communicating with one or more of the plurality of sensors to detect an activation.

10. The method of claim 9, further comprising determining a depth of loss of the articular surface based on one or more detected activations.

11. A monitoring system comprising:
a tibial plate configured to be secured to a tibia of a patient at least in part by bone cement between the tibial plate and the tibia, the tibial plate having a first contact sensor;
a tibial liner having a second contact sensor paired with the first contact sensor of the tibial plate during surgical placement, which pairing is indicative of an accurate fitting of the tibial liner with the tibial plate, and a plurality of additional sensors, each at a different depth relative to an articular surface of the tibial liner, and each configured to activate upon exposure at the articular surface of the tibial liner;
at least one additional sensor in or on the bone cement and configured to provide one of a measure of contact or a measure of pressure indicative of contact between the tibial plate and the tibia;
an accelerometer and a motion sensor positioned within the tibial plate, where the accelerometer is an acceleration sensor that measures acceleration and the motion sensor is a rotation sensor that measures rotation;
an electronic processor positioned within the tibial plate, where the electronic processor is electrically coupled to the acceleration sensor and to the rotation sensor;
a memory chip positioned within the tibial plate, where the memory chip is coupled to the electronic processor and is configured to store the measures of acceleration from the acceleration sensor and the measures of rotation from the rotation sensor;
an antenna configured to transmit the measures of acceleration and rotation from the memory chip to a location outside of the tibial plate; and
an interrogation module configured to communicate with one or more of:
the accelerometer to obtain measures of acceleration,
the motion sensor to obtain measures of rotation,
the first contact sensor of the tibial plate and the second contact sensor of the tibial liner to monitor changes in the accurate fitting,
the plurality of additional sensors of the tibial liner to detect wear in the tibial liner, and
the at least one additional sensor in or on the bone cement to monitor contact between the tibial plate and the tibia.

12. The monitoring system of claim 11, wherein the at least one additional sensor in or on the bone cement is a passive sensor configured to operate on power received from the interrogation module.

* * * * *